United States Patent
Israel et al.

(10) Patent No.: US 12,185,765 B2
(45) Date of Patent: Jan. 7, 2025

(54) VAPORIZATION DEVICE FOR VAPORIZING MULTIPLE LIQUIDS

(71) Applicant: Hava Health, Inc., Wilmington, DE (US)

(72) Inventors: Joshua John Israel, Belle Mead, NJ (US); Devin Michael Serago, Sewell, NJ (US); Jeffery William Domenighini, La Mesa, CA (US)

(73) Assignee: Hava Health, Inc., Wilmington, DE (US)

( * ) Notice: Subject to any disclaimer, the term of this patent is extended or adjusted under 35 U.S.C. 154(b) by 0 days.

(21) Appl. No.: 17/660,654

(22) Filed: Apr. 26, 2022

(65) Prior Publication Data

US 2022/0248767 A1 Aug. 11, 2022

Related U.S. Application Data

(63) Continuation of application No. 16/251,968, filed on Jan. 18, 2019, now Pat. No. 11,576,435.

(51) Int. Cl.
*A24F 40/50* (2020.01)
*A24F 40/10* (2020.01)
(Continued)

(52) U.S. Cl.
CPC ........... *A24F 40/50* (2020.01); *A61M 15/008* (2014.02); *A61M 15/06* (2013.01); *H05B 1/0244* (2013.01); *H05B 2203/021* (2013.01)

(58) Field of Classification Search
CPC .... A24F 40/50; A24F 40/65; A61B 2560/028; A61B 2562/0247; A61B 2562/0271;
(Continued)

(56) References Cited

U.S. PATENT DOCUMENTS

| 6,886,557 B2 | 5/2005 | Childers et al. |
| 9,271,528 B2 * | 3/2016 | Liu .................... A61M 11/042 |

(Continued)

FOREIGN PATENT DOCUMENTS

| EP | 2608686 | 6/2015 |
| GB | 2524779 | 7/2015 |

(Continued)

OTHER PUBLICATIONS

PCT International Application No. PCT/US20/13708, International Search Report and Written Opinion of the International Searching Authority, dated Apr. 16, 2020, 8 pages.
(Continued)

*Primary Examiner* — Abdullah A Riyami
*Assistant Examiner* — Thang H Nguyen
(74) *Attorney, Agent, or Firm* — DLA PIPER LLP (US)

(57) ABSTRACT

A vaporization device includes a first portion and a second portion. The first portion includes a first body defining a first interior volume, a first half of a split-pod, a second half of a split-pod, an opening, a first heating apparatus, and a second heating apparatus. The first half of the split-pod is configured to hold a nicotine-containing liquid. The second half of the split-pod is configured to hold a non-nicotine-containing liquid. The opening separates the first half from the second half of the split-pod. The first heating apparatus is dedicated to the first half. The second heating apparatus is dedicated to the second half. The second portion includes a second body defining a second interior volume and a computing system. The computing system is disposed within the second interior volume. The computing system is configured to vary an amount of current supplied to the first and second heating apparatuses.

19 Claims, 15 Drawing Sheets

(51) Int. Cl.
*A24F 40/65* (2020.01)
*A61M 15/00* (2006.01)
*A61M 15/06* (2006.01)
*H05B 1/02* (2006.01)

(58) Field of Classification Search
CPC .. A61B 5/0022; A61B 5/4833; A61M 11/042; A61M 15/0003; A61M 15/0066; A61M 15/008; A61M 15/06; A61M 2016/0024; A61M 2016/0027; A61M 2205/273; A61M 2205/3368; A61M 2205/3553; A61M 2205/3584; A61M 2205/3592; A61M 2205/505; A61M 2205/52; A61M 2205/6054; A61M 2205/609; G16H 20/13; G16H 50/20; G16H 80/00; H05B 1/0244; H05B 2203/021
See application file for complete search history.

(56) References Cited

U.S. PATENT DOCUMENTS

| | | | |
|---|---|---|---|
| 10,039,320 B2* | 8/2018 | Cameron | A24F 40/30 |
| 10,251,423 B2* | 4/2019 | Mamoun | G05D 7/0676 |
| 10,292,427 B2* | 5/2019 | Cameron | A24F 40/53 |
| 10,842,189 B1* | 11/2020 | Hermiz | A24F 40/46 |
| 11,298,473 B2* | 4/2022 | Goldstein | A61M 15/06 |
| 2011/0265806 A1* | 11/2011 | Alarcon | A24F 40/485 |
| | | | 131/273 |
| 2013/0284192 A1* | 10/2013 | Peleg | A24F 40/53 |
| | | | 131/329 |
| 2013/0319439 A1* | 12/2013 | Gorelick | A24F 40/65 |
| | | | 131/329 |
| 2013/0340775 A1* | 12/2013 | Juster | H04L 12/1827 |
| | | | 131/273 |
| 2014/0366898 A1* | 12/2014 | Monsees | A24F 40/30 |
| | | | 131/329 |
| 2015/0149886 A1* | 5/2015 | Homer | G06F 40/166 |
| | | | 715/234 |
| 2015/0310760 A1* | 10/2015 | Knotts | G09B 19/00 |
| | | | 434/236 |
| 2016/0081393 A1* | 3/2016 | Black | H04L 67/10 |
| | | | 392/404 |
| 2016/0089508 A1* | 3/2016 | Smith | A61M 15/0085 |
| | | | 128/202.21 |
| 2016/0157524 A1 | 6/2016 | Bowen et al. | |
| 2016/0219938 A1* | 8/2016 | Mamoun | G05B 15/02 |
| 2016/0325055 A1* | 11/2016 | Cameron | A24F 40/50 |
| 2016/0331034 A1* | 11/2016 | Cameron | A61M 15/0003 |
| 2016/0331037 A1* | 11/2016 | Cameron | A24F 40/50 |
| 2017/0027232 A1* | 2/2017 | Scheck | A24F 40/51 |
| 2017/0181471 A1* | 6/2017 | Phillips | A61M 15/06 |
| 2017/0181474 A1 | 6/2017 | Cameron | |
| 2017/0181475 A1 | 6/2017 | Cameron | |
| 2017/0251721 A1 | 9/2017 | Rostami et al. | |
| 2018/0043114 A1 | 2/2018 | Bowen et al. | |
| 2018/0325176 A1* | 11/2018 | Burseg | A24F 40/30 |
| 2019/0124982 A1* | 5/2019 | Atkins | A61M 11/042 |
| 2019/0357596 A1 | 11/2019 | Blick et al. | |
| 2020/0016344 A1 | 1/2020 | Scheck et al. | |
| 2020/0022416 A1* | 1/2020 | Alarcon | A24F 40/57 |
| 2020/0229500 A1* | 7/2020 | Israel | A24F 40/50 |
| 2021/0268208 A1* | 9/2021 | Hatton | A61M 11/044 |
| 2021/0307392 A1* | 10/2021 | Rosser | A24F 40/42 |
| 2021/0346617 A1* | 11/2021 | Wagner | H01R 13/26 |
| 2021/0360974 A1* | 11/2021 | Mironov | H05B 6/105 |

FOREIGN PATENT DOCUMENTS

| | | |
|---|---|---|
| WO | 2013/152873 | 10/2013 |
| WO | 2015/038981 | 3/2015 |

OTHER PUBLICATIONS

Office Action for GB Patent Application No. GB2111012.7, mailed Oct. 9, 2023, 2 pages.

Search Report for GB Patent Application No. GB2310299.9, mailed Oct. 6, 2023, 1 page.

* cited by examiner

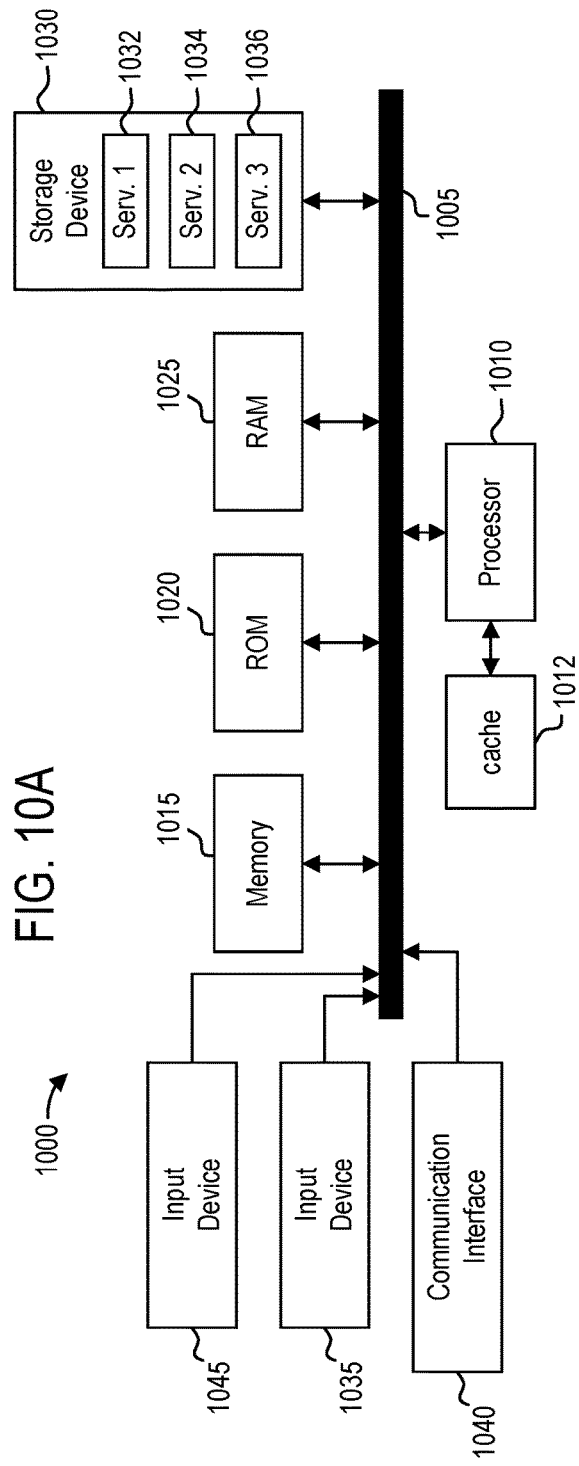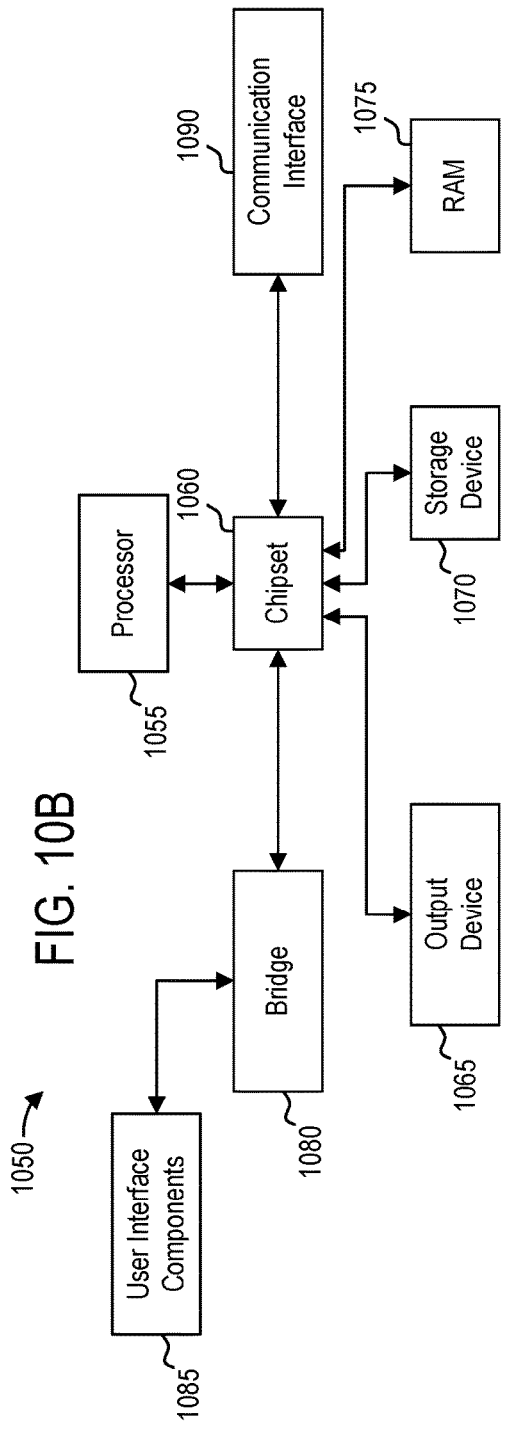

VAPORIZATION DEVICE FOR VAPORIZING MULTIPLE LIQUIDS

CROSS-REFERENCE TO RELATED APPLICATION INFORMATION

This is a continuation of U.S. patent application Ser. No. 16/251,968, filed Jan. 18, 2019, which is incorporated herein by reference in its entirety.

FIELD OF THE DISCLOSURE

The present disclosure generally relates to a vaporization device and a system for implementing a smoking cessation plan utilizing the vaporization device.

BACKGROUND

Vaporizer devices have been frequently used as a cigarette replacement or as a means to wean users of cigarettes. For example, vaporizer devices may be a battery operated device that is specially configured to mimic or simulate the feeling of smoking a cigarette. However, rather than burning actual tobacco, the vaporizer device is configured to burn a liquid solution, thereby creating a vapor inhalable by the user. Such liquid solutions may include a nicotine-containing substances similar to that of cigarettes.

SUMMARY

Embodiments disclosed herein generally relate to a system and method for facilitating a smoking cessation plan. In some embodiments, a vaporization device is disclosed herein. The vaporization device includes a first portion and a second portion. The second portion is selectively coupled with the first portion. The first portion includes a first body, a first half of a split-pod, a second half of a split-pod, an opening, a first heating apparatus, and a second heating apparatus. The first body defines a first interior volume. The first half of the split-pod and the second half of the split-pod are formed in the first interior volume. The first half of the split-pod is configured to hold a nicotine-containing liquid. The second half of the split-pod configured to hold a non-nicotine-containing liquid. The opening is formed in the first body. The opening separates the first half of the split-pod from the second half of the split-pod. The first heating apparatus is dedicated to the first half of the split-pod. The second heating apparatus is dedicated to the second half of the split-pod. The second portion includes a second body and a computing system. The second body defines a second interior volume. The computing system is disposed within the second interior volume. The computing system is configured to vary an amount of current supplied to the first heating apparatus and the second heating apparatus.

In some embodiments, a smoking cessation system is disclosed herein. The smoking cessation system includes a vaporization device and a server system. The vaporization device includes a first half of a split-pod and a second half of a split-pod. The first half of the split-pod is configured to hold a nicotine-containing liquid. The second half of the split-pod is configured to hold a non-nicotine-containing liquid. The vaporization device is configured to deliver a vapor mixture. The vapor mixture includes a first vapor formed from the non-nicotine-containing liquid and a second vapor formed from the nicotine-containing liquid. The server system is in communication with the vaporization device. The server system is configured to generate a smoking cessation plan for the vaporization device based on at least usage statistics associated with the vaporization device.

In some embodiments, a computer-implemented method of facilitating a smoking cessation plan is disclosed herein. A server system generates an initial smoking cessation plan based on one or more inputs provided by a client device in communication with a vaporization device. The initial smoking cessation plan includes one or more phases. Each phase is associated with a predefined ratio of a vapor mixture for the vaporization device to deliver to a user. The server system transmits the initial smoking cessation plan to the client device. The server system receives one or more streams of usage statistics associated with the user's use of vaporization device. The server system analyzes the one or more streams of usage statistics to determine whether the user's use of vaporization device is in accordance with the initial smoking cessation plan. The server system determines that the user's use of the vaporization device deviates from the initial smoking cessation plan. The server system modifies the initial smoking cessation plan based on the usage statistics.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrated only typical embodiments of this disclosure and are therefore not to be considered limiting of its scope, for the disclosure may admit to other equally effective embodiments.

FIG. 10A is a block diagram illustrating a computing device, according to example embodiments.

FIG. 10B is a block diagram illustrating a computing device, according to example embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

One or more embodiments disclosed herein generally relate to a vaporization device and a system for implementing a smoking cessation plan utilizing the vaporization device. The vaporization device may include a first portion that is selectively coupled to a second portion. The first portion may include a body. The body may include a split-pod configuration. For example, the body may include a split-pod with the first half of the split-pod configured to hold a nicotine-containing substance and a second half of the split-pod configured to hold a non-nicotine-containing substance. Each half of the split-pod may include a respective heating apparatus, configured to create a vapor mixture from the nicotine-containing substance and the non-nicotine-containing substance. The second portion may include a computing system disposed therein. The computing system may be configured to vary the amount of current provided to each respective heating apparatus, such that a predefined ratio of nicotine-containing substance to non-nicotine-containing substances is delivered to the user. Such ratio may be generated as part of an overall smoking cessation plan stored on the vaporization device.

Figure 1:
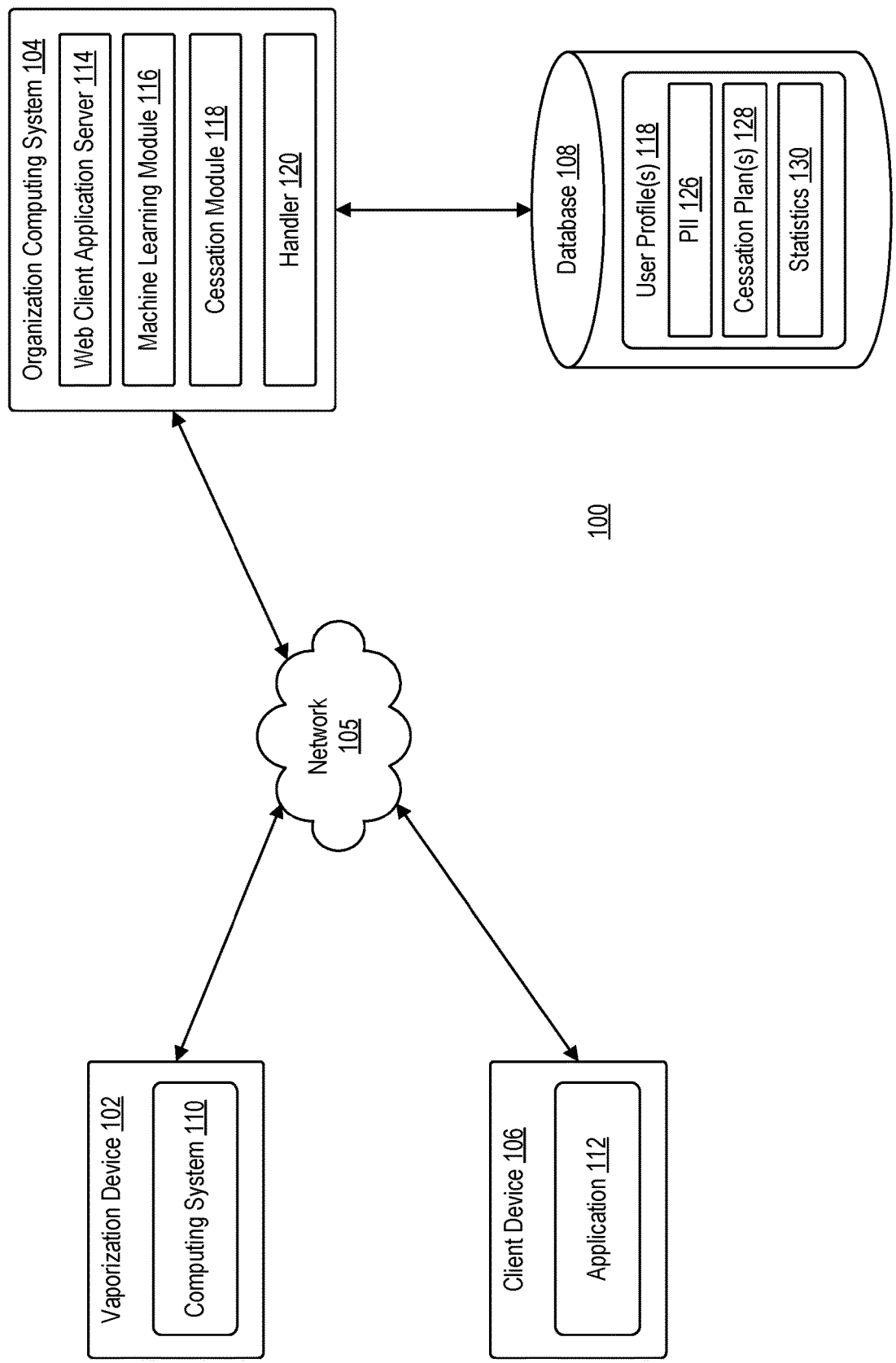
FIG. 1 is a block diagram illustrating a computing environment, according to example embodiments.

The vaporization device may be configured to communicate with a user's client device (e.g., mobile phone). For example, vaporization device may provide client device with the user's usage statistics. Such usage statistics may include a number of uses of vaporization device, as well as the duration of each use. Client device may provide the usage statistics to a server system. The server system may adjust the smoking cessation plan based on the usage statistics provided by the client device. For example, if a user is too heavily relying on the vaporization device (e.g., higher usage rate than expected), the server system may adjust the smoking cessation plan accordingly, FIG. 1 is a block diagram illustrating a computing environment 100, according to example embodiments. Computing environment 100 may include vaporization device 102, organization computing system 104, and client device 106 communicating via network 105.

Network 105 may be of any suitable type, including individual connections via the Internet, such as cellular or Wi-Fi networks. In some embodiments, network 105 may connect terminals, services, and mobile devices using direct connections, such as radio frequency identification (RFID), near-field communication (NFC), Bluetooth™, low-energy Bluetooth™ (BLE), Wi-Fi™ ZigBee™, ambient backscatter communication (ABC) protocols, USB, WAN, or LAN. Because the information transmitted may be personal or confidential, security concerns may dictate one or more of these types of connection be encrypted or otherwise secured. In some embodiments, however, the information being transmitted may be less personal, and therefore, the network connections may be selected for convenience over security.

Network 105 may include any type of computer networking arrangement used to exchange data. For example, network 105 may include any type of computer networking arrangement used to exchange information. For example, network 105 may be the Internet, a private data network, virtual private network using a public network and/or other suitable connection(s) that enables components in computing environment 100 to send and receive information between the components of environment 100.

Client device 106 may be operated by a user. For example, client device 106 may be a mobile device, a tablet, a desktop computer, or any computing system having the capabilities described herein. Client device 106 may belong to or be provided to a user or may be borrowed, rented, or shared. Users may include, but are not limited to, individuals such as, for example, subscribers, clients, prospective clients, or customers of an entity associated with organization computing system 104, such as individuals who have obtained, will obtain, or may obtain a product, service, or consultation from an entity associated with organization computing system 104.

Client device 106 may include at least application 112. Application 112 may be representative of a web browser that allows access to a website or a stand-alone application. Client device 106 may access application 112 to access functionality of organization computing system 104. Client device 106 may communicate over network 105 to request a webpage, for example, from web client application server 114 of organization computing system 104. For example, client device 106 may be configured to execute application 112 to access content managed by web client application server 114. The content that is displayed to client device 106 may be transmitted from web client application server 114 to client device 106, and subsequently processed by application 110 for display through a graphical user interface (GUI) of client device 106.

Client device 106 may communicate with vaporization device 102. For example, client device 106 may communicate with vaporization device 102 via network 105. Vaporization device 102 may be a split-pod vaporization device configured to deliver a vapor mixture formed from a nicotine-containing substance and a non-nicotine-containing substance. Vaporization device 102 is discussed in further detail below in conjunction with FIGS. 2-6.

Vaporization device 102 may include computing system 110. Computing system 110 may be configured to communicate with client device 106. In some embodiments, computing system 110 may be further configured to communicate with organization computing system 104. Computing system 110 may be configured to track user of vaporization device 102 may an end user. For example, computing system 110 may track a number of uses of vaporization device 102 and a duration of each user. In some embodiments, vaporization device 102 may transmit the usage information to client device 106. Client device 106 may, in turn, transmit the usage information to organization computing system 104. In some embodiments, vaporization device 102 may transmit usage information directly to organization computing system 104.

Organization computing system 104 may include at least web client application server 114, a machine learning module 116, a cessation module 118, and handler 120. Each of machine learning module 116, cessation module 118, and handler 120 may be comprised of one or more software modules. The one or more software modules may be collections of code or instructions stored on a media (e.g., memory of organization computing system 104) that represent a series of machine instructions (e.g., program code) that implements one or more algorithmic steps. Such machine instructions may be the actual computer code the processor of organization computing system 104 interprets to implement the instructions or, alternatively, may be a higher level of coding of the instructions that is interpreted to obtain the actual computer code. The one or more software modules may also include one or more hardware components. One or more aspects of an example algorithm may be performed by the hardware components (e.g., circuitry) itself, rather as a result of the instructions.

Cessation module 118 may be configured to communicate with client device 106. In some embodiments, cessation module 118 may be configured to communicate with vaporization device 102. Cessation module 118 may receive usage information from vaporization device 102. Cessation module 118 may work in conjunction with machine learning module 120 to generate a smoking cessation plan for each user based, in part, on user input and usage information. For example, cessation module 118 may work in conjunction with machine learning module 120 to generate a cessation plan that includes a ratio of nicotine-containing substance to non-nicotine-containing substance to deliver to a user. Based off received usage information, cessation module 118 may work in conjunction with machine learning module 120 to update the cessation plan for each user.

Machine learning module 116 may include one or more instructions to train a prediction model used by cessation module 118. To train the prediction model, machine learning module 120 may receive, as input, usage activity of each user. In some embodiments, machine learning module 120 may further receive, as input, one or more parameters specified by each user via application 112. Machine learning module 116 may implement one or more machine learning algorithms to train the prediction model. For example, machine learning module 116 may use one or more of a decision tree learning model, association rule learning model, artificial neural network model, deep learning model, inductive logic programming model, support vector machine model, clustering mode, Bayesian network model, reinforcement learning model, representational learning model, similarity and metric learning model, rule based machine learning model, and the like.

Account handler 120 may be configured to manage an account associated with each user. For example, account handler 120 may be configured to communicate with database 108. As illustrated, database 108 may include one or more user profiles 124. Each user profile 124 may correspond to a user with an account with organization computing system 104. Each user profile 124 may include at least one or more of personal identification information 126, a cessation plan 128, and statistics 130. Personal identification information 126 may include information associated with the user. In some embodiments, personal identification information 126 may include a name, home address, billing address, mailing address, telephone number, e-mail address, social security number, and the like. Cessation plan 128 may correspond to a cessation plan generated for each user by cessation module 118 and machine learning module 116. Cessation plan 128 may include one or more phases, wherein each phase of cessation plan 128 may include a specific ratio of nicotine-containing substance to non-nicotine-containing substance in a vapor mixture as well as a duration for each phase. Statistics 130 may include one or more statistics associated with a user's usage. Such statistics may include usage information tracked by computing system 110.

Figure 2:
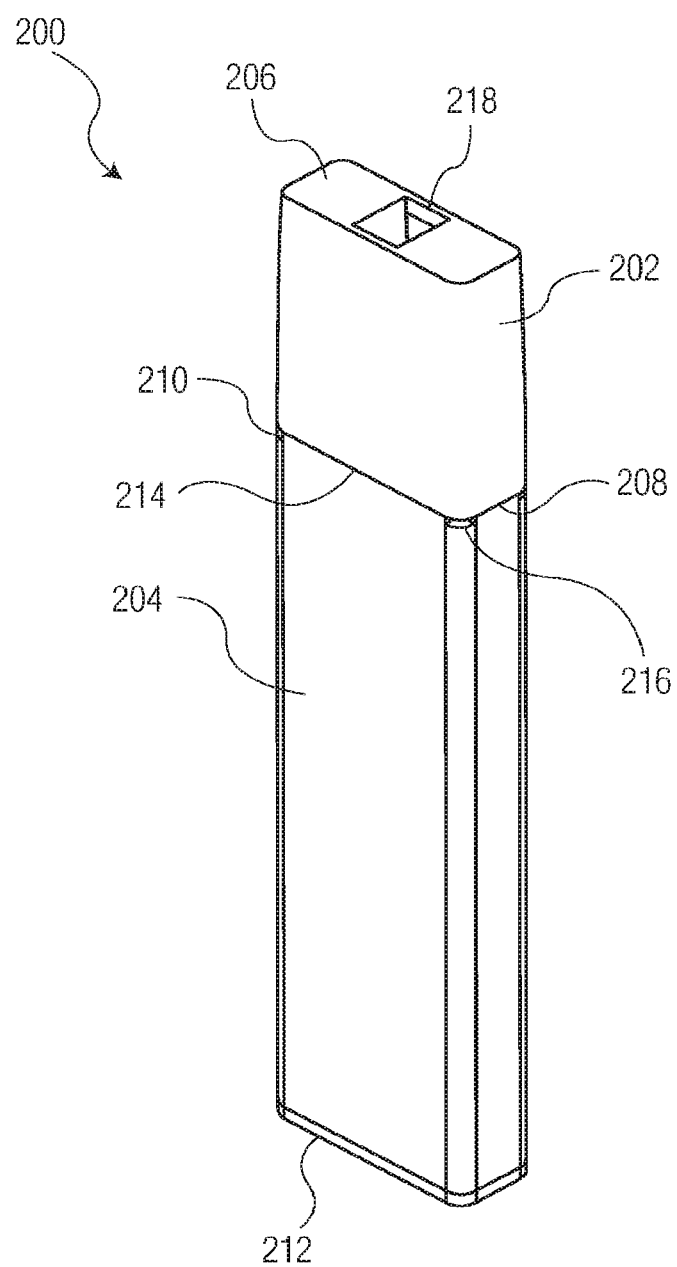
FIG. 2 is a perspective view of a vaporization device, according to example embodiments.

FIG. 2 is a perspective view of a vaporization device 200, according to example embodiments. Vaporization device 200 may be an example of vaporization device 102 discussed above, in conjunction with FIG. 1. As illustrated, vaporization device 200 may include a first portion 202 and a second portion 204. First portion 202 may be selectively coupled with second portion 204.

First portion 202 may generally include a first end 206 and a second end 208, opposite first end 206. First end 206 may include an opening 218 formed therein. In some embodiments, first portion 202 may taper from second end 208 to first end 206. As discussed in further detail below, first portion 202 may be configured to store one or more fluids used for delivery of a vapor mixture to users of vaporization device 200. For example, first portion 202 may be configured to store at least two liquids: a non-nicotine containing liquid and a nicotine containing liquid. In operation, a vapor mixture formed from at least a portion of the non-nicotine containing liquid and the nicotine containing liquid may be delivered to user of vaporization device 200.

First portion 202 may be formed from a thermoplastic material (e.g., high-temperature thermoplastic material). Generally, first portion 202 may be formed from a food-safe, chemical (e.g., oil) resistant material. Exemplary materials may include, but are not limited to, nylon-based plastic (or equivalent), polyphenylene sulfide (PPS), polyether ether ketone (PEEK), polyetherimide (PEI), and the like.

Second portion 204 may generally include a first end 210 and a second end 212, opposite first end. Although not shown in this particular figure, second end 212 may include a charging slot formed therein. Exemplary charging slots may include, but are not limited to, universal serial bus (USB) port, lightening port, and the like. As discussed in further detail below, second portion 204 may be configured to house one or more electronic components of vaporizer device 202.

Second portion 204 may be formed from extruded aluminum alloy, a material having an anodized or powder coating, and the like.

As illustrated in FIG. 2, when in selective communication, first portion 202 may create an interface 214 with second portion 204. Interface 214 may not be uniform about vaporizer device 210. For example, formed between first portion 202 and second portion 204 may be one or more air passages 216. Each air passage 216 may allow air to flow from outside vaporizer device 200 to an interior volume defined therein. For example, when a user inhales via opening 218, air may be pulled within vaporizer device 200 via one or more air passages 216.

Generally, first portion 202 may be configured as a disposable component of vaporizer device 102. For example, first portion 202 may be disposed by end user when first portion 202 no longer contains at least one of a nicotine-containing substance or a non-nicotine-containing substance. However, rather than having the user physically refill first portion 202, the user may purchase a new first portion 202 for use with vaporizer device 102.

In some embodiments, first portion 202 may be self-destructing. In other words, first portion 202 may be configured such that a user cannot tamper with first portion 202 (e.g., re-fill or re-use first portion 202, take liquid out of first portion 202, etc.).

Figure 3A:
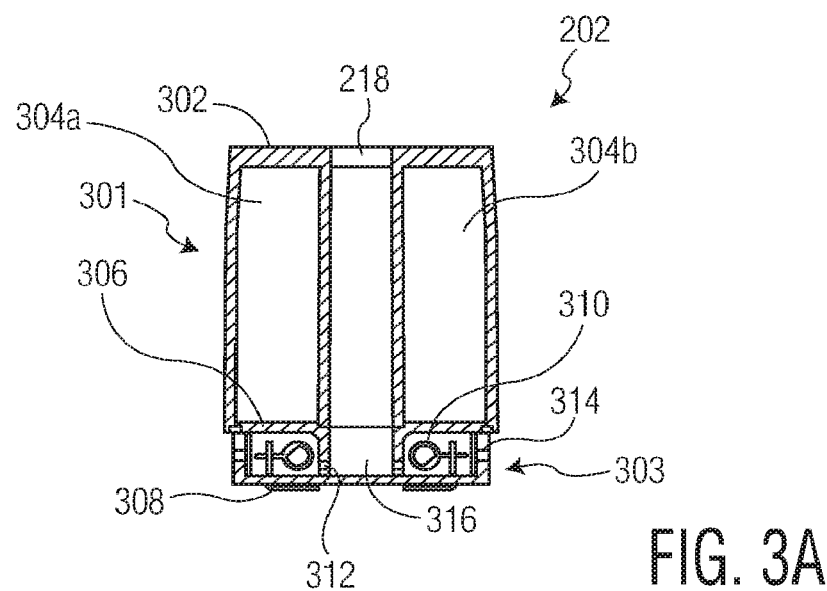
FIG. 3A is a cross-sectional view of first portion of vaporizer device, according to example embodiments.

FIG. 3A is a cross-sectional view of first portion 202 of vaporizer device 200, according to example embodiments. First portion 202 may include a body 302. Body 302 may include a first region 301 and second region 303. First region 301 may include a split-pod formed therein. For example, first region 301 may include a first half of a split-pod 304a and a second half of a split-pod 304b. First half the pod 304a may be separated from second half of the split-pod 304b via opening 218, which may extend from first end 206 of first portion 202 to second region 302. Both first half of the split-pod 304a and second half of the split-pod 304b may be configured to hold a liquid. For example, first half of the split-pod 304a may be configured to hold a nicotine-containing liquid; second half of the split-pod 304b may be configured to hold a non-nicotine-containing liquid.

Second portion 304 of body 302 may include one or more electric contacts 308 and one or more heating coils 310. In some embodiments, each of one or more heating coils 308 may be positioned adjacent a respective half of the split-pod 304a, 304b. For example, second portion 304 of body 302 may include a first heating coil 310 dedicated to first half of the split-pod 304a and a second heating coil 310 dedicated to second half of the split-pod 304b. Each heating coil 310 may be configured to heat the liquid contained in a respective half of the split-pod 304a, 304b to create a vapor mixture. Each heating coil 310 may be formed from a metal material that is used for resistive heating. Exemplary metal materials may include, but are not limited to, Nichrome, KANTHAL®, stainless steel, and the like.

Each electrical contact 308 may be configured to deliver power to each heating coil 310. For example, each electric contact 308 may be configured to deliver a defined amount of power to each coil 308, such that a specific ratio of non-nicotine-containing liquid to nicotine-containing liquid is vaporized. In some embodiments, each electrical contact 308 may be positioned adjacent a respective half of the entire split-pod 304a, 304b. For example, second portion 304 of body 302 may include a first electrical contact 308 dedicated to a first heating coil 310 for first half of the split-pod 304a and a second electrical contact 308 dedicated to a second heating coil 310 for the second half of the split-pod 304b.

As illustrated, each electrical contact 308 may be configured to support a respective heating coil 310. For example, each electric contact 308 may include an opening (not shown) formed therein. Electrical coil 310 may at least partially extend within the opening, such that electrical coil 310 may be supported by electrical contact 308.

Body 302 may further include one or more divider walls 306. Each of divider wall 306 may be positioned in such a way as to separate each heating coil 310 from a respective half of the split-pod 304a, 304b. For example, as illustrated, a first divider wall 306 may be positioned between first half of the split-pod 304a and first heating coil 310 and a second divider wall 306 may be positioned between second half of the split-pod 304b and second heating coil 310. Each divider wall 306 may include an opening (not shown) formed therein. Each opening may be formed as to allow passage of a wicking material between each half of the split-pod 304a, 304b and a respective heating coil 310. Wicking material may be used to deliver fluid from a respective half of the split-pod 304a, 304b to a respective heating coil 310. Exemplary wicking materials may include, but are not limited to, silica, cotton, or other porous materials).

Body 302 may further include a mixing chamber 316, one or more vapor vents 312, and one or more air vents 314 formed therein. Mixing chamber 316 may be defined within second region 303. Mixing chamber 316 may be in fluid communication with opening 218. For example, mixing chamber 316 may be formed in second region 303, such that mixing chamber 316 may separate each respective set of electrical contacts 308 and heating coils 310. Each vapor vent 312 may be formed within an interior of first portion 202. For example, each vapor vent 312 may be formed proximate a respective heating coil 310. In operation, vapor formed from fluid in one half of the split-pod 304a may enter mixing chamber 316 via a first vapor vent 312, and vapor formed from fluid in second half of the split-pod 304b may enter mixing chamber 316 via a second vapor vent 312. Within mixing chamber 316, vapor formed from a non-nicotine-containing fluid may mix with vapor formed from a nicotine-containing fluid to form a vapor mixture. The vapor mixture may be delivered to an end user via opening 218.

Each air vent 314 may be formed in body 302. For example, as illustrated, each air vent 314 may be formed such that each air vent 314 may provide fluid communication between an interior of body 302 and an exterior of body 302. One or more air vents 314 may be configured to draw ambient air into vaporizer device 200. For example, one or more air vents 314 may be configured to draw ambient air into vaporizer device 200 via one or more air passages 216, upon inhalation of an end user.

Figure 3B:
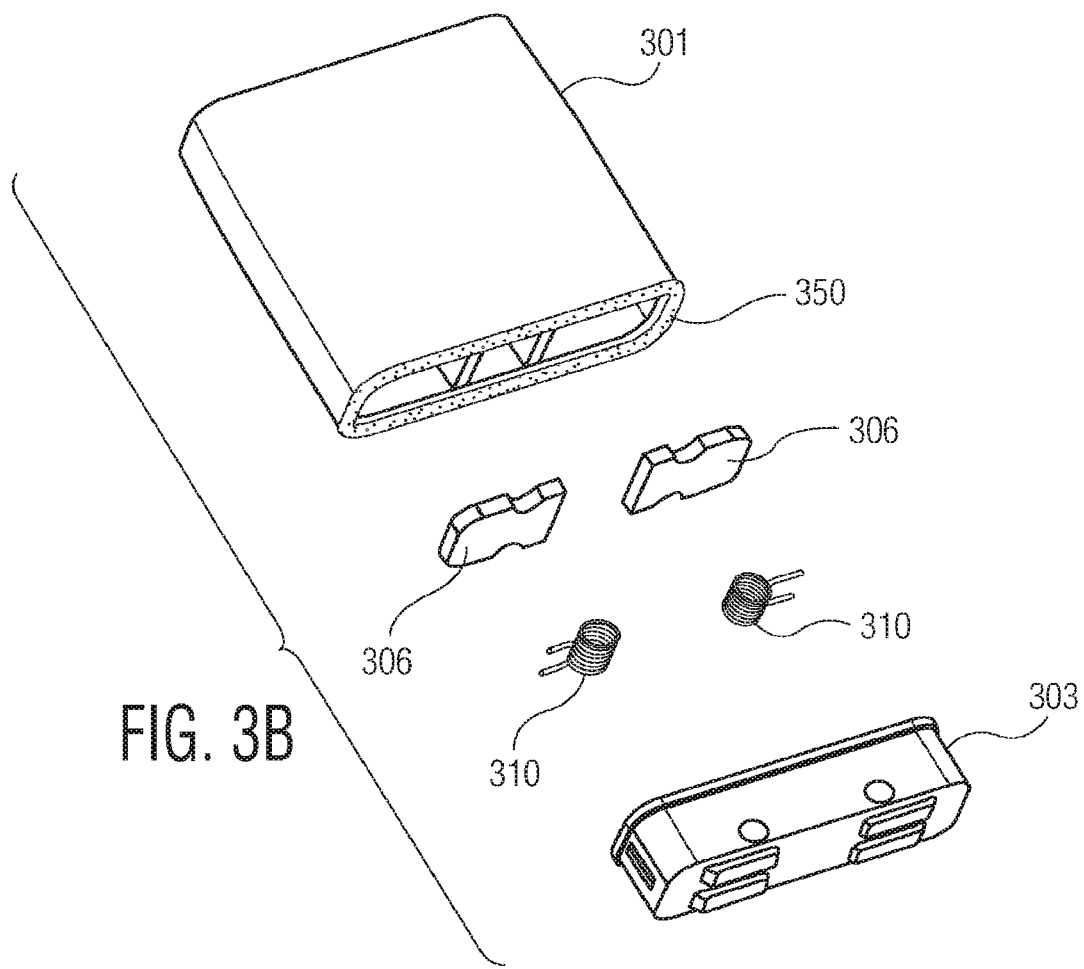
FIG. 3B is a cross-sectional view of first portion of vaporizer device, according to example embodiments.

FIG. 3B is an exploded view of first portion 202 of vaporizer device 200, according to example embodiments. As discussed above, in some embodiments, first portion 202 may be self-destructing. In other words, first portion 202 may be configured such that a user cannot tamper with first portion 202 (e.g., re-fill or re-use first portion 202, take liquid out of first portion 202, etc.).

As illustrated, first region 301 is shown detached from second region 303. Between first region 301 and second region 303 are one or more divider walls 306 and heating coils 310. To configure first portion 202 such that first portion 202 is tamper-proof, a sealant 350 may be used to couple first region 301 to second region 303. In some embodiments, sealant 350 may be applied to first region 301, such that after first region 301 and second region 303 are attached, sealant 350 prevents disassembly of second region 303 from first region 301. Sealant 350 may be any sealant able to prevent fluid leakage from first region 301. Exemplary sealants may include, but are not limited to silicon, epoxy, a combination of the two, or any other suitable material.

Figure 3C:
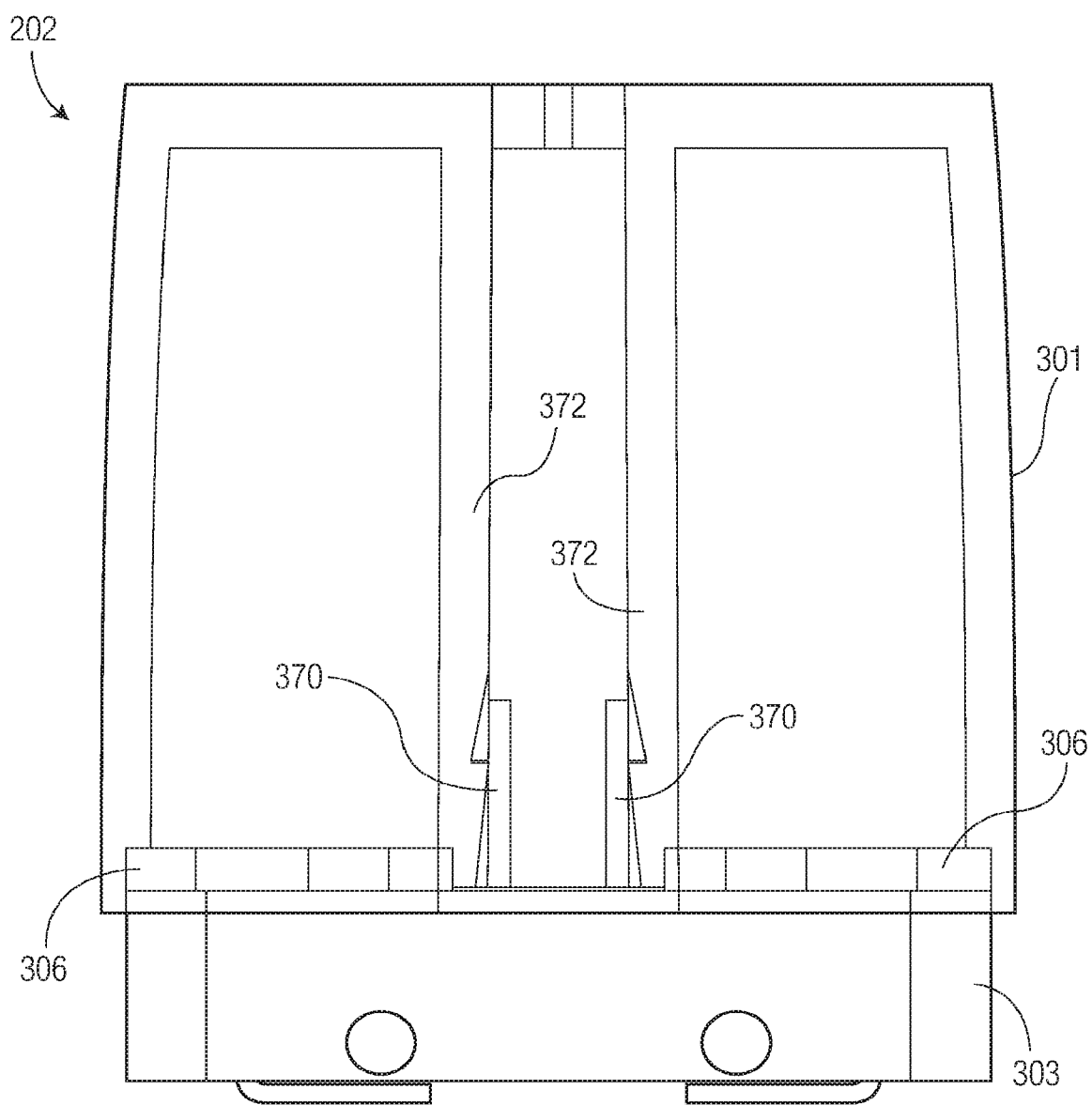
FIG. 3C is a cross-sectional view of first portion of vaporizer device, according to example embodiments.

FIG. 3C is a front perspective view of first portion 202 of vaporizer device 200, according to example, embodiments. As discussed above, in some embodiments, first portion 202 may be self-destructing. In other words, first portion 202 may be configured such that a user cannot tamper with first portion 202 (e.g., re-fill or re-use first portion 202, take liquid out of first portion 202, etc.).

As illustrated, first region 301 is shown attached to second region 303. Second region 303 may include one or more internal snap hooks 370 integrated therein. As illustrated, each of the one or more internal snap hooks 370 may secure second region 303 to first region 301 by interfacing with one or more internal walls 372 of first region 301. As such, use of one or more internal snap hooks 370 may result in a single-use first portion 202 (i.e., single-use pod). In some embodiments, first portion 202 may implement a combination of one or more snap hooks 370 and sealant 350 to prevent tampering with first region 301.

Figure 4A:
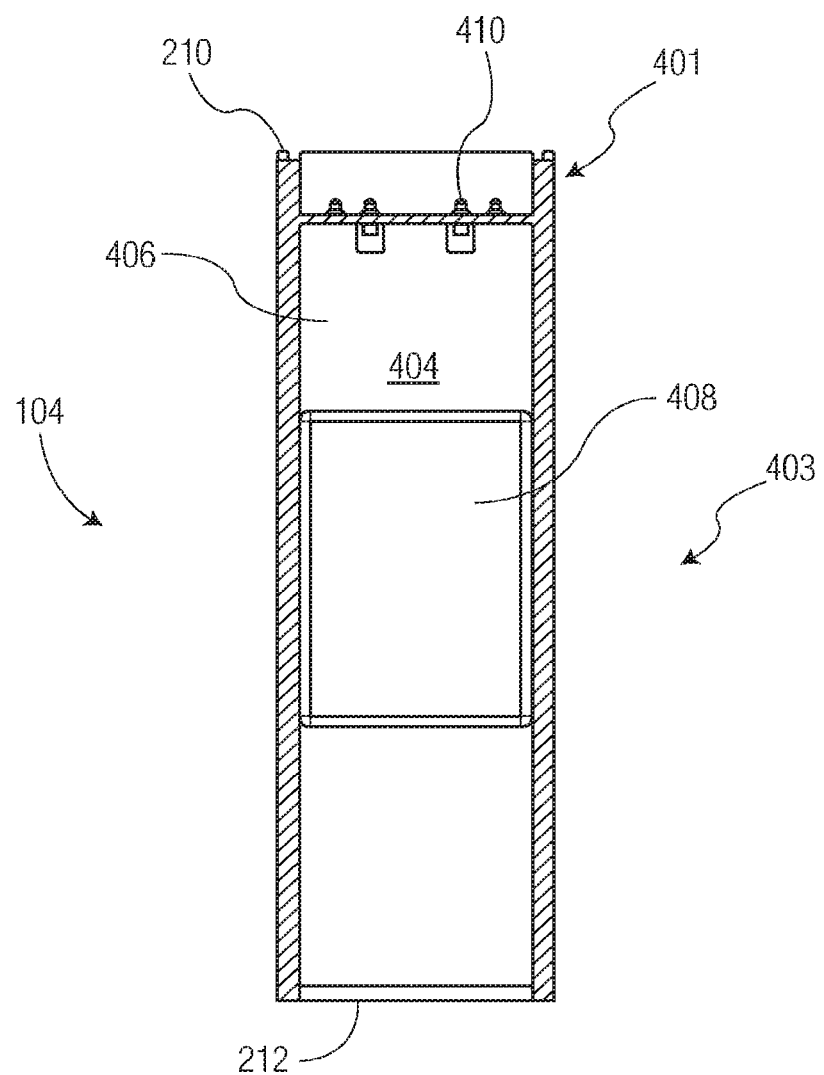
FIG. 4A is a cross-sectional view of second portion of vaporizer device, according to example embodiments.

FIG. 4A is a cross-sectional view of second portion 204 of vaporizer device 200, according to example embodiments. Second portion 204 may include a body 402. Body 402 may include a first region 401 and second region 403. First region 401 may be configured to receive first portion 202 of vaporizer device 200. For example, when selectively coupled, second region 303 of first portion 202 of vaporizer device 200 may be positioned at least partially within first region 401 of second portion 204 of vaporizer device 200.

Second region 403 may define interior volume 404. Disposed within interior volume 404 may be at least computing system 110. Computing system 110 may include a printed circuit board 406 and a power source 408. Printed circuit board 406 may include at least one or more of power control circuitry, current sensing circuitry, voltage sensing circuitry, charging interface, battery charging circuitry, network interface (e.g., radio frequency identification (RFID) module, near-field communication (NFC) module, Bluetooth™ module, low-energy Bluetooth™ (BLE) module, Wi-Fi™ adapter, ZigBee™ module, etc.), microcontroller, and one or more safety mechanisms.

Microcontroller may be configured to communicate with a remote computing server. For example, microcontroller may be configured to communicate user consumption information to a remote computing server and receive, from the remote computing server, dosage instructions. The dosage instructions (described in further detail below) provide the microcontroller with instructions directed to a target temperature of each heating coil 310 and a duration each heating coil 310 is heated. The dosage instructions may be a part of a larger cessation plan generated by remote computing server.

Microcontroller may instruct the power control circuitry regarding the amount of power to be provided to one or more electrical contacts 308. Power control circuitry may be configured to control the amount of power provided by power source 408 to one or more electrical contacts 308. For example, temperature of heating coils 310 may be measured using the resistance change of the coil, and implementing a feedback look with the microcontroller to adjust the power output to meet the target temperature (e.g., proportional-integral-derivative (PID) control loop). In some embodiments, power control circuitry may be a metal oxide silicon field effect transistor (MOSFET). The amount of power provided by power source 408 to each electrical contact 308 affects the amount of vapor produced by first portion 202 of vaporizer device 200. In some embodiments, power source 408 may be a re-chargeable battery (e.g., 3.7 V battery).

In some embodiments, microcontroller may use a regression-based algorithm programmed locally on each device, which may be loaded to microcontroller via application 112 executing on client device 106 associated with vaporization device 200. The regression-based algorithm may include instructions on how and when to reduce a user's nicotine intake. In some embodiments, for each user, there may be a control period in which organization computing system 104 learns and understands a user's smoking behaviors. For example, organization computing system 104 may learn the amount of time, milligrams of nicotine taken per day, and the number of times vaporization device 200 is used. This data may be used to design each user's cessation plan.

For each user, the variables that are stored may be:

Start date ($t_0$)—this may represent the date when the user started the smoking cessation program.

k—this may represent a constant that will be used to control how steep the regression will be for the patient. k may be a negative value. For example, k may be in the range between about −0.05 and −0.5. The higher the absolute value, the steeper the regression of the nicotine, and the quicker the patient will quit smoking. In some embodiments, the default value of k may be about −0.2.

Control period (c)—this may represent the length of the initial period, during which no regression takes place, but the patient's current smoking habits are being monitored. In some embodiments, the maximum nicotine does may be applied during each hit.

After the control period, the following values may be calculated:

Average initial daily dose ($D_0$)—this may represent the average daily nicotine dose during the control period, calculated from the hits made during that period.

Current daily dose ($D_n$)—this may represent the daily nicotine dose for the $n^{th}$ day ($t_n$). This may be calculated using: $D_n = D_0 * e(t_n - t_0 - c) * k$.

Average number of hits ($h_e$)—this may represent the average number of hits made per day during the program up until the $n^{th}$ day (including the hits made during the control period).

Current hit dose ($d_n$)—this may represent the nicotine dose for the current hit, calculated using the formula:

$$d_n = \frac{D_n}{h_n}.$$

In some embodiments, the program may end when $d_n$ falls below a threshold value (e.g., 0.005 mg).

Printed circuit board 406 may further include one or more contacts 410 coupled thereto. As illustrated, one or more contacts 410 may take the form of a pin-shaped contact. In some embodiments, one or more contacts 410 may be soldered to printed circuit board 406. One or more contacts 410 may be configured to contact each electrical contact 308, when first portion 202 and second portion 204 are in selective communication. One or more contacts 410 may be configured to transfer current provided by battery 408 to one or more electrical contacts to raise a temperature of one or more heating coils 308. In some embodiments, each contact 410 may be spring actuated to ensure solid contact with each electrical contact 308.

Further, although not shown, in some embodiments, second portion 204 may include a fingerprint sensor located on an exterior surface of body 402. Fingerprint sensor may be in communication with computing system 110. For example, when a user wants to use vaporization device 102, the user may unlock vaporization device 102 using fingerprint sensor located thereon.

Figure 4B:
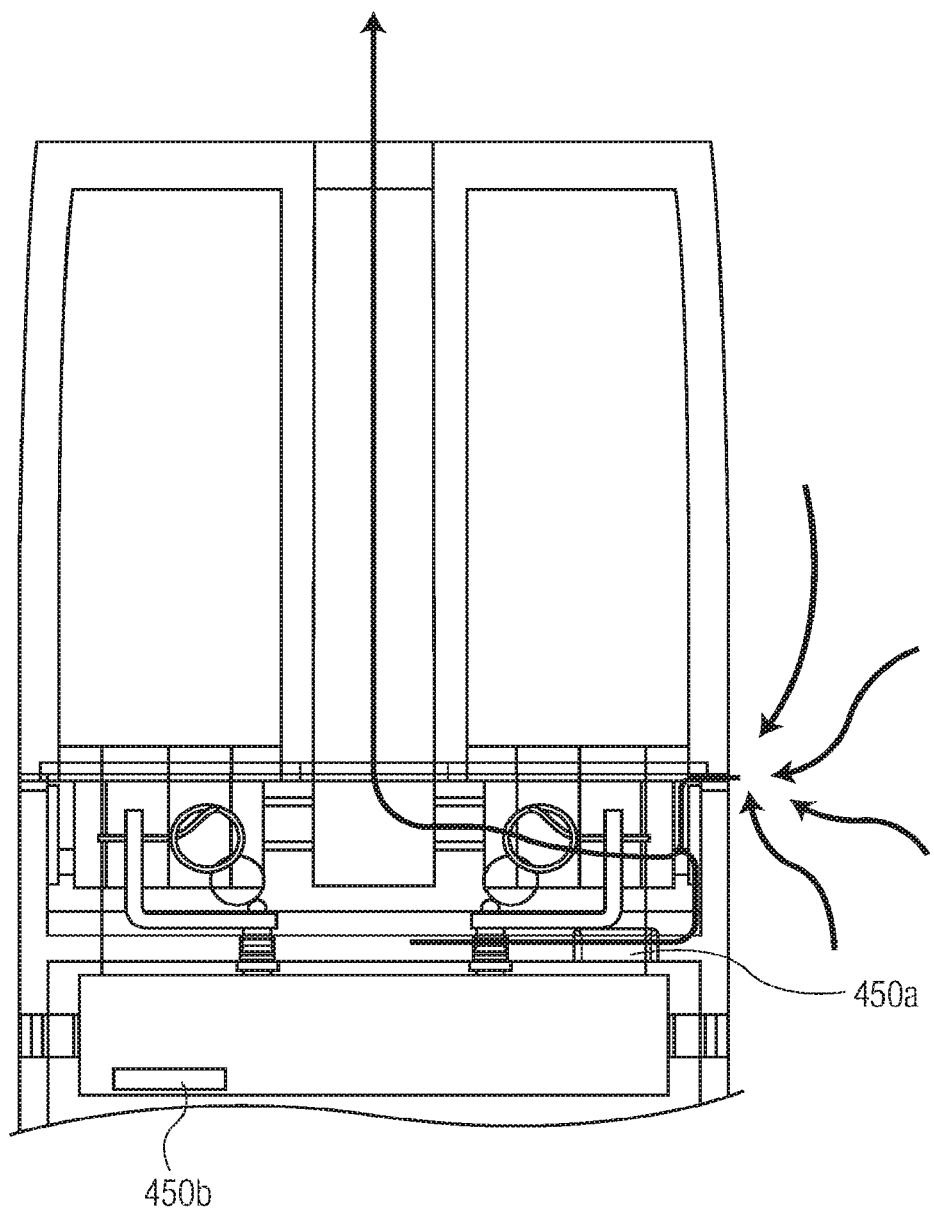
FIG. 4B is a cross-sectional view of second portion of vaporizer device, according to example embodiments.

FIG. 4B is a partial cross-sectional view of vaporization device 200, according to example embodiments. As illustrated, first portion 202 is selectively coupled to second portion 204. In some embodiments, such as that shown in FIG. 4B, second portion 204 may include one or more pressure sensors 450a, 450b (generally, "pressure sensor 450") disposed therein. For example, second portion 204 may include a first pressure sensor 450a selectively positioned in the path of airflow during inhalation and a second pressure sensor 450b placed in the main housing. First pressure sensor 450a may be positioned in second portion 204, such that first pressure sensor 450a is exposed to airflow during inhalation as a result of the pressure drop in interior volume 404.

Second pressure sensor 450b may be configured to observe atmospheric pressure. Second pressure sensor 450b may be used in conjunction with first pressure sensor 450b to determine the differential pressure between atmosphere and that of the inhalation path. By doing so, accuracy is improved, most notable in situations when vaporization device 200 is taken to locations with different atmospheric pressures.

Figure 5:
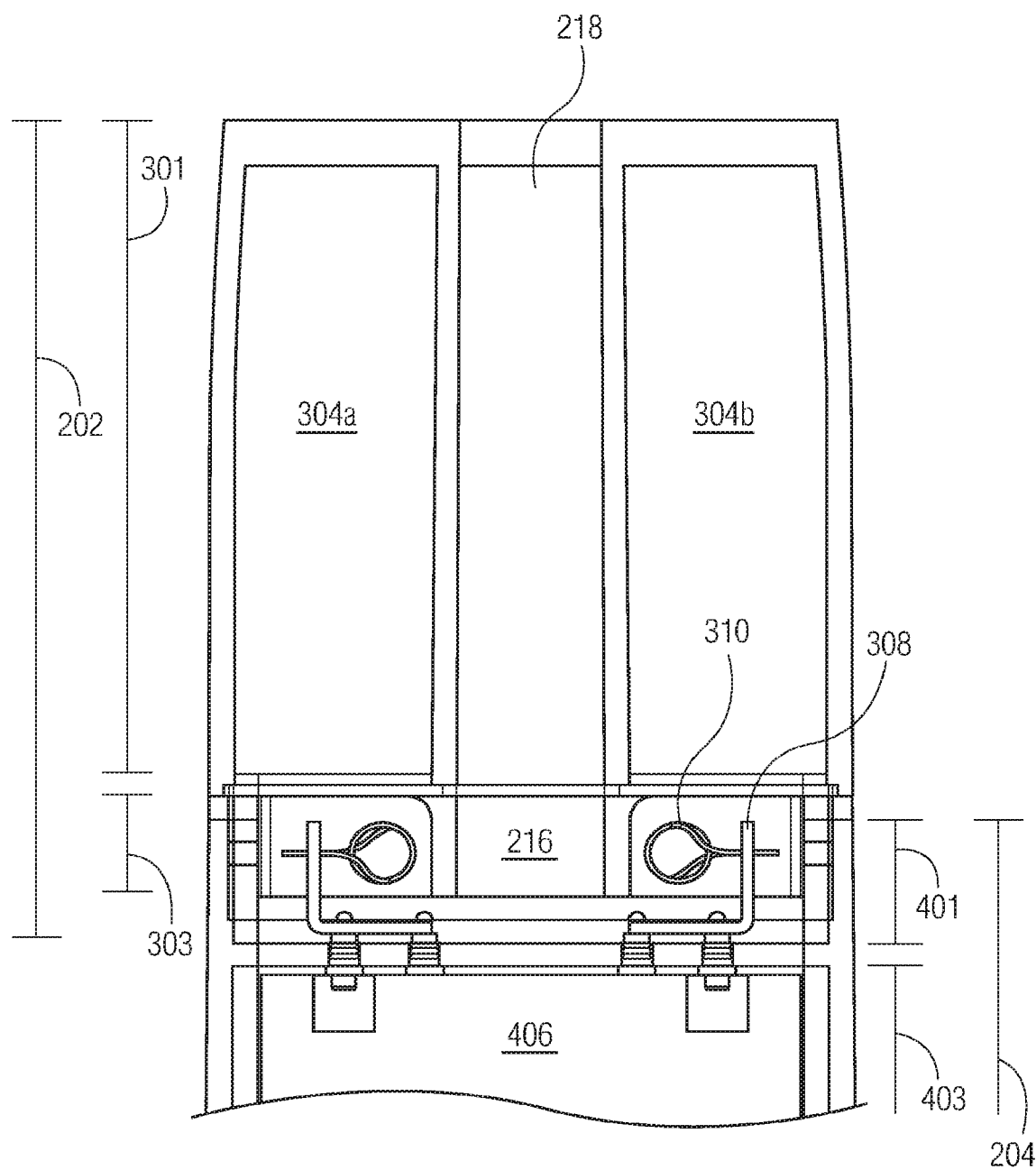
FIG. 5 is a partial cross-sectional view of a vaporization device, according to example embodiments.

FIG. 5 is a partial cross-sectional view of a vaporization device 200, according to example embodiments. As illustrated, first portion 202 is selectively coupled to second portion 204. Second region 303 of first portion 202 may be positioned at least partially within first region 401 of second portion 204. In some embodiments, mating between first portion 202 and second portion 204, via second region 303 and first region 401, may be secured via natural friction, a lever tab, a snap hook, a magnet, and the like. When selectively coupled, one or more contacts 410 may be in physical contact with one or more electrical contacts 308.

Figure 6:
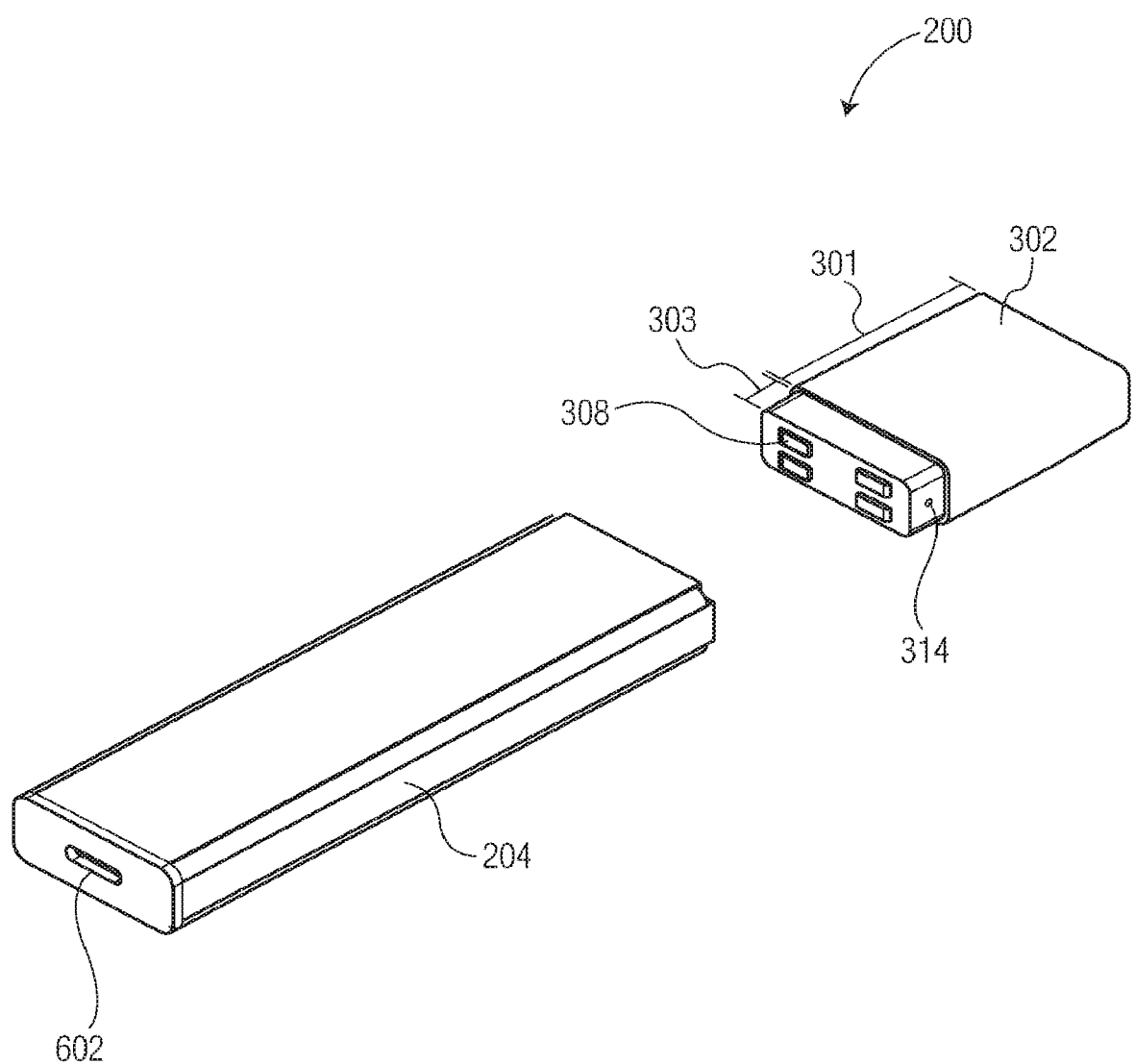
FIG. 6 is a perspective view of vaporization device, according to example embodiments.

FIG. 6 is a perspective view of vaporization device 200, according to example embodiments. As illustrated, first portion 202 is detached from second portion 204. As may not have been visible in previous Figures, another view of first region 301 and second region 303 of first portion 202 is shown. Further, as previously recited but now shown in detail, second portion 204 may include changing slot 602 formed in second end 212 of second portion 204. Exemplary charging slots may include, but are not limited to, universal serial bus (USB) port, lightening port, and the like.

Figure 11:
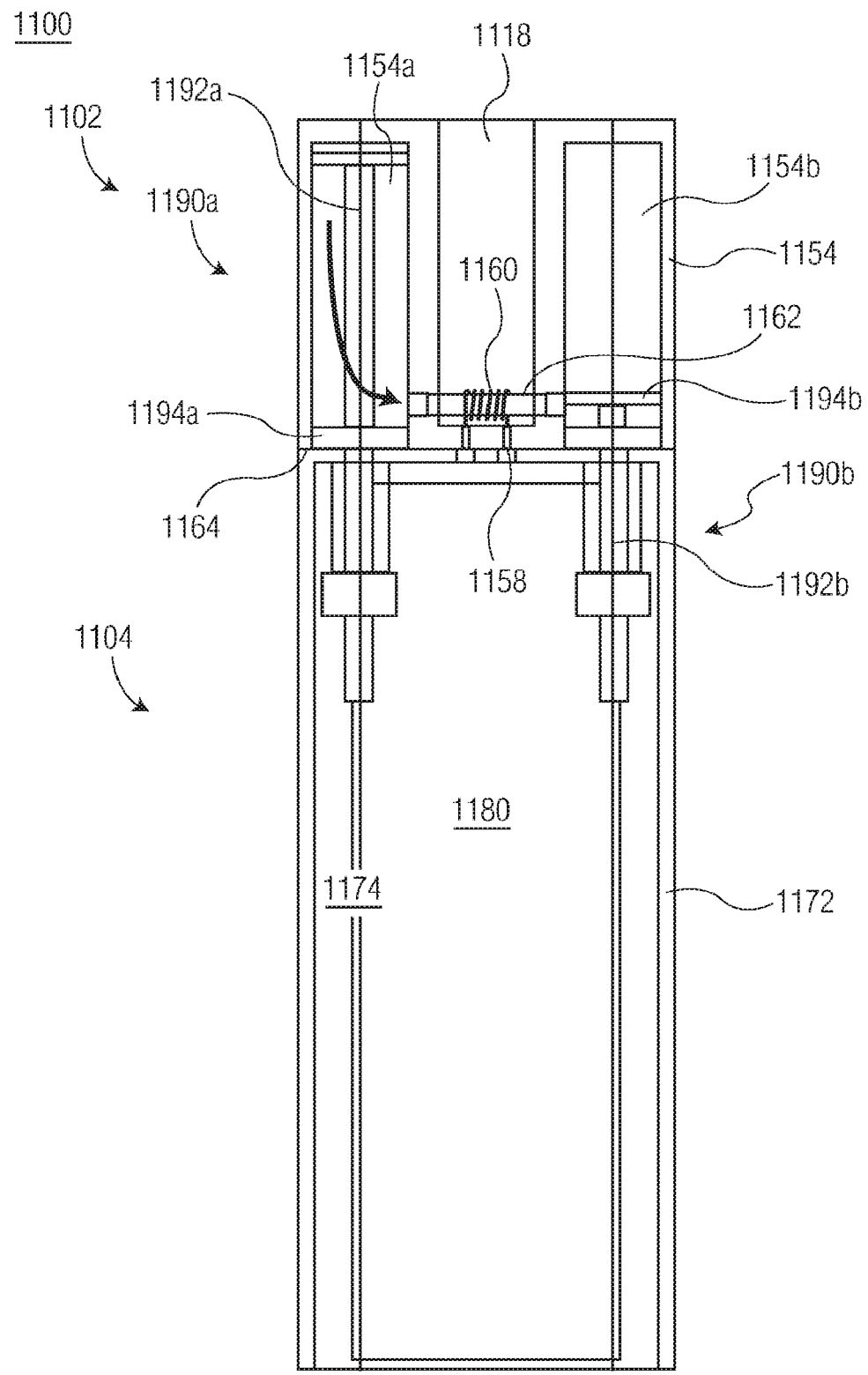
FIG. 11 is a perspective view of a vaporization device, according to example embodiments.

FIG. 11 is a perspective view of a vaporization device 1100, according to example embodiments. Vaporization device 1100 may be an example of vaporization device 102 discussed above, in conjunction with FIG. 1. As illustrated, vaporization device 1100 may include a first portion 1102 and a second portion 1104. First portion 1102 may be selectively coupled with second portion 1104. First portion 1102 may include an opening 1118 formed therein.

As discussed in further detail below, first portion 1102 may be configured to store one or more fluids used for delivery of a vapor mixture to users of vaporization device 1100. For example, first portion 1102 may be configured to store at least two liquids: a non-nicotine containing liquid and a nicotine containing liquid. In operation, a vapor mixture formed from at least a portion of the non-nicotine containing liquid and the nicotine containing liquid may be delivered to user of vaporization device 1100.

As discussed in further detail below, second portion 1104 may be configured to house one or more electronic components of vaporizer device 1102. When in selective communication, first portion 1102 may create an interface 1114 with second portion 1104. Interface 1114 may not be uniform about vaporizer device 1110. For example, formed between first portion 1102 and second portion 1104 may be one or more air passages 1116. Each air passage 1116 may allow air to flow from outside vaporizer device 1100 to an interior volume defined therein. For example, when a user inhales via opening 1118, air may be pulled within vaporizer device 1100 via one or more air passages 1116.

First portion 1102 may include a body 1152. Body 1152 may include a split-pod formed therein. For example, body 1152 may include a first half of a split-pod 1154a and a second half of a split-pod 1154b. First half the pod 1154a may be separated from second half of the split-pod 1154b via opening 1118, which may extend through first portion 1102. Both first half of the split-pod 1154a and second half of the split-pod 1154b may be configured to hold a liquid. For example, first half of the split-pod 1154a may be configured to hold a nicotine-containing liquid; second half of the split-pod 1154b may be configured to hold a non-nicotine-containing liquid.

Body 1152 may further include one or more electrical contacts 1158, a heating coil 1160, and a wick mechanism 1162. In some embodiments, heating coil 1160 may be positioned proximate each half of the split-pod 1154a, 1154b. For example, heating coil 1160 may be positioned between first half of split-pod 1154a and second half of split-pod 1154b. In some embodiments, heating coil 1160 may be positioned about wick mechanism 1162. For example, heating coil 1160 may be wrapped around wick mechanism 1162. Heating coil 1160 may be configured to heat the liquid contained in each respective half of the split-pod 304a, 304b to create a vapor mixture. Heating coil 1160 may be formed from a metal material that is used for resistive heating. Exemplary metal materials may include, but are not limited to, Nichrome, KANTHAL®, stainless steel, and the like.

Each electrical contact 1158 may be configured to deliver power to heating coil 1160. For example, each electric contact 1158 may be configured to deliver a defined amount of power to each coil 308, such that a specific amount of liquid is vaporized.

Body 1152 may further include one or more air vents 1164. Each air vent 1164 may be formed in body 1152. For example, as illustrated, each air vent 1164 may be formed such that each air vent 1164 may provide fluid communication between an interior of body 1152 and an exterior of body 1152. One or more air vents 1164 may be configured to draw ambient air into vaporizer device 1100.

Second portion 1104 may include a body 1172. Body 1172 may define interior volume 1174. Disposed within interior volume 1174 may be at least computing system 1180. Computing system 1180 may be substantially similar to computing system 110 discussed above in conjunction with FIG. 4A.

As illustrated, vaporization device 1100 may include one or more piston assemblies 1190a, 1190b (generally "piston assembly 1190") that extends from first portion 1102 to second portion 1104. Each piston assembly 1190 may be configured to selectively deliver a dosage of liquid to a user of vaporization device 1100. Each piston assembly may include a rod 1192a, 1192b (generally "rod 1192") which is configured to move linearly and a plate 1194a, 1194b (generally "plate 1194") coupled to each rod 1192a, 1192b, respectively. As illustrated, piston assembly 1190a may be positioned within first half of split-pod 1154a. Piston assembly 1190a may extend from first half of split-pod 1154a into interior volume 1174 of second portion 1104. Piston assembly 1190b may be positioned within second half of split-pod 1154b. Piston assembly 1190b may extend from second half of split-pod 1154b into interior volume 1174 of second portion 1104.

In operation, computing system 1180 may control each piston assembly 1190, such that each rod 1192 may move linearly to control the amount of fluid provided to wick mechanism 1162. The distance each rod 1192 moves is translated to an amount of fluid provided to wick mechanism 1162. For example, the movement of rod 1192a down within first half of split-pod 1154a may push fluid in first half of split-pod 1154a down and out to wick mechanism 1162. Computing system 1180 may control each piston assembly 1190 individually, such that a certain ratio of nicotine-containing fluid to non-nicotine-containing fluid is delivered to the user.

In operation, air may be drawn from outside of vaporization device 1100 via one or more air vents 1164, such that the air flows past heating coil 1160 and wick mechanism 1162, into opening 1118, and into the user's mouth.

Figure 7A:
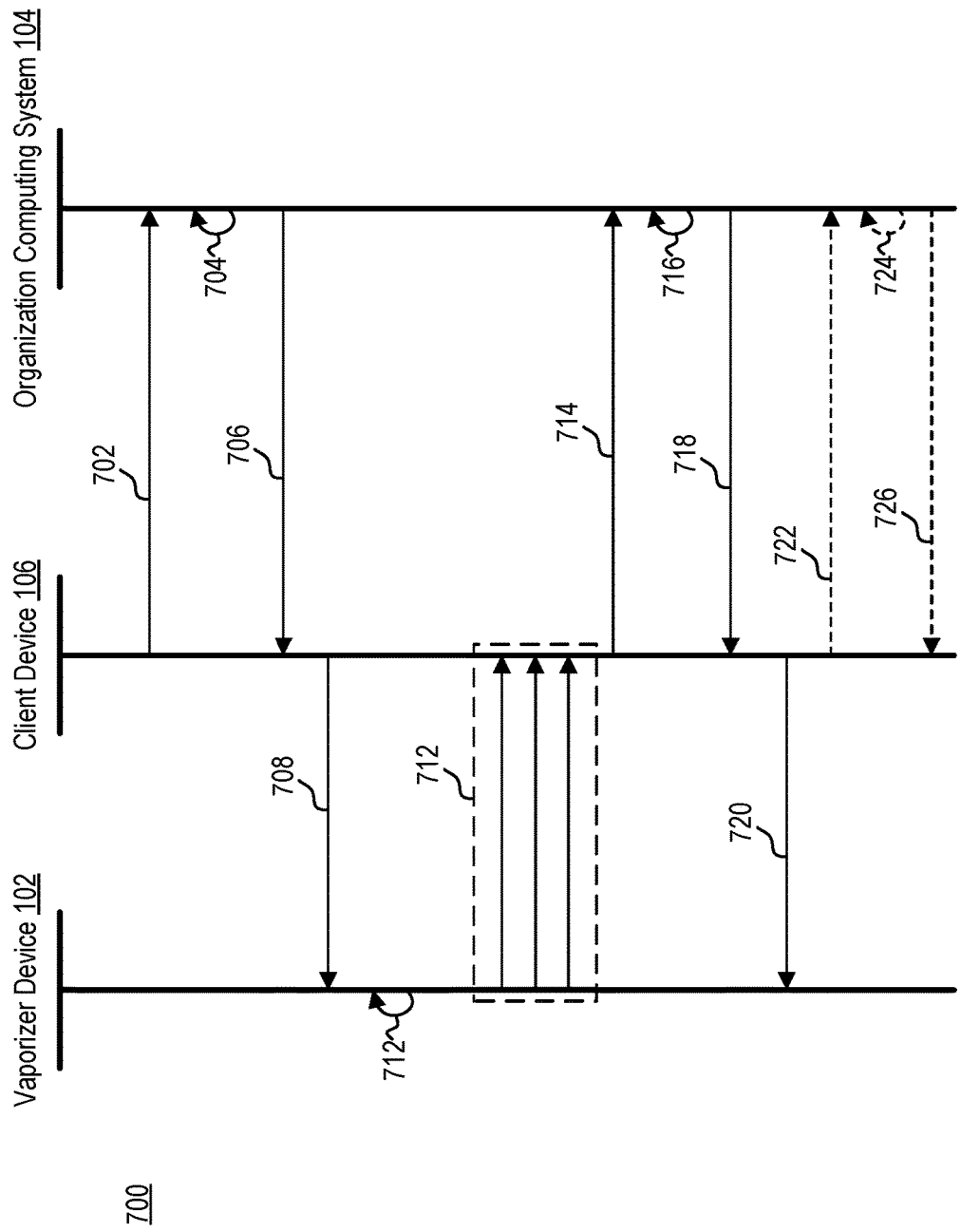
FIG. 7A is a block diagram illustrating a method of generating a smoking cessation plan, according to example embodiments.

FIG. 7A is a logical diagram illustrating a method 700 of generating a smoking cessation plan, according to exemplary embodiments. For example, method 700 of generating a smoking cessation plan may involve use of vaporization device 102 discussed above in conjunction with FIGS. 1-6. Method 700 may begin at step 702.

At step 702, client device 702 may access organization computing system 104 to initialize a smoking cessation plan. For example, client device 702 may access functionality of organization computing system 104 via application 112. In some embodiments, initializing a smoking cessation plan may include an end user to register a vaporization device 102 and enroll in a plan. Further, in some embodiments, initializing a smoking cessation plan includes client device 106 transmitting initializing information. Such initializing information may include, but is not limited to, a user's age, gender, smoking habits (e.g., how many times per day, how many packs per week, how long the user has smoked for, etc.), occupation, smoking cessation goals, and the like.

At step 704, organization computing system 104 may generate a smoking cessation plan for the user. In some embodiments, organization computing system 104 may generate a smoking cessation plan based on the initializing information. Cessation module 118 may leverage a prediction model generated by machine learning module 116 to generate a smoking cessation plan for the user. For example, cessation module 118 may provide one or more items of initializing information to prediction model to generate the smoking cessation plan. As such, the user's smoking cessation plan may be individualized to the user's attributes and goals. The smoking cessation plan may include one or more phases, such that each phase may include a specific ratio of nicotine-containing substance to non-nicotine-containing substance in a vapor mixture. Over time (e.g., as the user progress through the various phases), the ratio of substances within the vapor mixture may change, until a user is almost entirely consuming a vapor formed from the non-nicotine-containing substance.

At step 706, organization computing system 104 may transmit the smoking cessation plan to client device 106 of the user. In some embodiments, organization computing system 104 may provide client device 106 with access to the smoking cessation plan via one or more application programming interfaces (APIs) that allow client device 106 to access the smoking cessation plan.

At step 708, client device 106 may communicate the smoking cessation plan to vaporizer device 102. For example, client device 106 may interface with computing system 110 in vaporization device 102, such that vaporization device 102 may store at least a portion of the smoking cessation plan in memory. The portion of the smoking cessation plan transmitted from client device 106 to computing system 110 may include instructions as to how much power to deliver to each heating coil 310. Accordingly, computing system 110 may control the amount of current provided by a battery source to each electrical contact 308.

At step 710, vaporization device 102 may deliver a vapor mixture formed from a predefined ratio of a nicotine-containing substance and a non-nicotine containing substance to the end user. For example, when a user attempts to consume a vapor mixture, computing system 110 may deliver a predefined amount of current to each electric contact 308 to heat each heating coil 310. Heating each heating coil 310 to a predetermined level aims in producing an amount of vapor from each half of the split-pod 304a, 304b, such that the predefine ratio is achieved.

At step 712, vaporization device 102 may transmit user data to client device 106. For example, vaporization device 102 may transmit usage statistics that include a number of inhalations and a duration for each inhalation to client device 106. In some embodiments, vaporization device 102 may transmit usage statistics in real-time (or near real-time), whenever vaporization device 102 is connected to client device 106 via one or more networks. In some embodiments, vaporization device 102 may transmit usage statistics in one or more batches. For example, vaporization device 102 may transmit usage statistics periodically (e.g., daily).

At step 714, client device 106 may forward the user data to organization computing system 104. For example, client device 106 may provide the user data to organization computing system 106, such that organization computing system 104 may analyze the user's usage of vaporization device 102, and update the smoking cessation plan accordingly.

At step 716, organization computing system 104 may receive the user data from client device 106. Organization computing system 104 may analyze the user date to determine whether the smoking cessation plan should be adjusted. For example, cessation module 118 may be configured to provide the user data, as input, to prediction model to determine whether the initial smoking cessation plan should be adjusted. Such adjustments may be made, for example, if the user is consuming more vapor mixture than previously expected. The adjustments may results in an extension of certain phases to the smoking cessation plan, such that the user is more slowly weaned off the nicotine-containing substance.

At step 718, organization computing system 104 may transmit the updated smoking cessation plan to client device 106 of the user. In some embodiments, organization computing system 104 may provide client device 106 with access to the updated smoking cessation plan via one or more APIs that allow client device 106 to access the updated smoking cessation plan.

At step 720, client device 106 may communicate the updated smoking cessation plan to vaporizer device 102. For example, client device 106 may interface with computing system 110 in vaporization device 102, such that vaporization device 102 may store at least a portion of the updated smoking cessation plan in memory. The portion of the smoking cessation plan transmitted from client device 106 to computing system 110 may include updated instructions as to how much power to deliver to each heating coil 310. Accordingly, computing system 110 may control the amount of current provided by a battery source to each electrical contact 308.

In some embodiments, logical diagram 700 may further include one or more steps 722-726. At step 722, client device 106 may access functionality of organization computing system 104 to access user statistics. For example, client device 106 may access application 112 to view usage statistics corresponding to vaporization device 102. Client device 106 may request access to usage statistics by requesting access via a log-in prompt. For example, via client device 106, a user may log into his or her account.

At step 724, organization computing system 104 may receive the request from client device 106 to view usage statistics corresponding to vaporization device 102 and the user's account. For example, upon receiving a request from client device 106, organization computing system 104 may generate one or more graphical user interfaces (GUIs) that visually display usage statistics to end user. Exemplary GUIs are discussed below in conjunction with FIGS. 8A and 8B.

At step 726, organization computing system 104 may provide client device 106 with access to the one or more GUIs. For example, in some embodiments, organization computing system 104 may transmit the one or more GUIs to client device 106 for rendering and display. In some embodiments, organization computing system 104 may provide client device 106 with access to the one or more GUIs via one or more APIs that allow client device 106 to access the one or more GUIs to display the usage statistics.

Figure 7B:
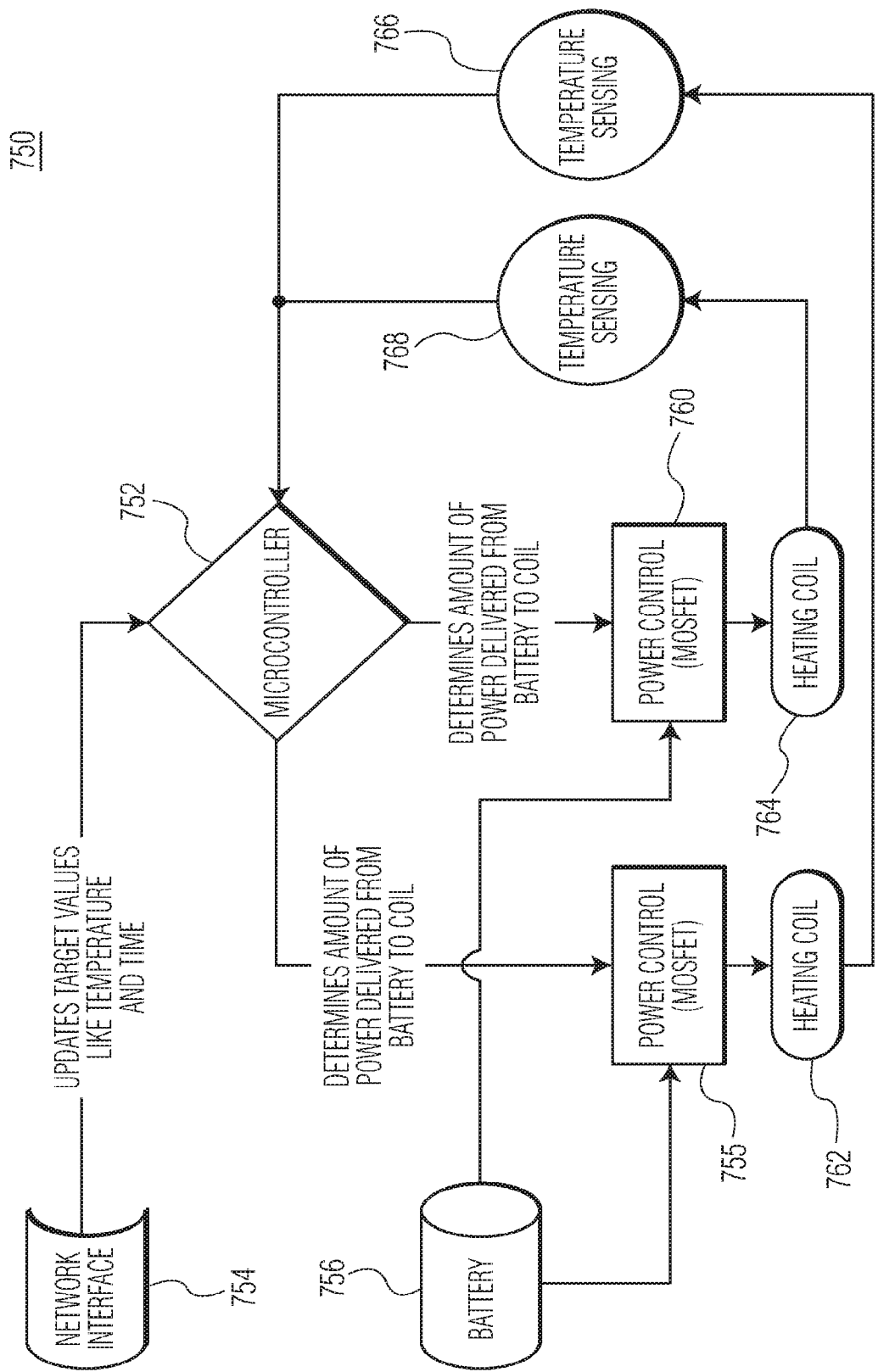
FIG. 7B is a block diagram illustrating one or more operations associated with use of vaporization device, according to example embodiments.

FIG. 7B is a block diagram 750 illustrating one or more operations associated with use of vaporization device 200, according to example embodiments. As shown, block diagram 750 includes a microcontroller 752, a network interface 754, a battery 756, a first power control 758, a second power control 760, a first heating coil 762, a second heating coil 764, a first temperature sensor 766, and a second temperature senor 768.

As illustrated, a user, via network interface 754, may update target values like temperature and time for vaporization device usage. Such target values may be input to microcontroller 752. Microcontroller 752 may determine the amount of power to be delivered from battery 756 to each heating coil 762, 764, based on the target values. First power controller 758 (e.g., first MOSFET) may control the amount of power provided to first heating coil 762, in accordance with instructions received from microcontroller 752. Second power controller 760 (e.g., second MOSFET) may control the amount of power provided to second heating coil 764, in accordance with instructions received from microcontroller 752. First temperature sensor 766 may monitor the temperature of first heating coil 762, and provide the temperature readings to microcontroller 752, thus creating a first feedback loop between microcontroller 752 and first heating coil 762. Second temperature sensor 768 may monitor the temperature of second heating coil 764, and provide the temperature readings to microcontroller 752, thus creating a second feedback loop between microcontroller 752 and second heating coil 764.

Figure 8A:
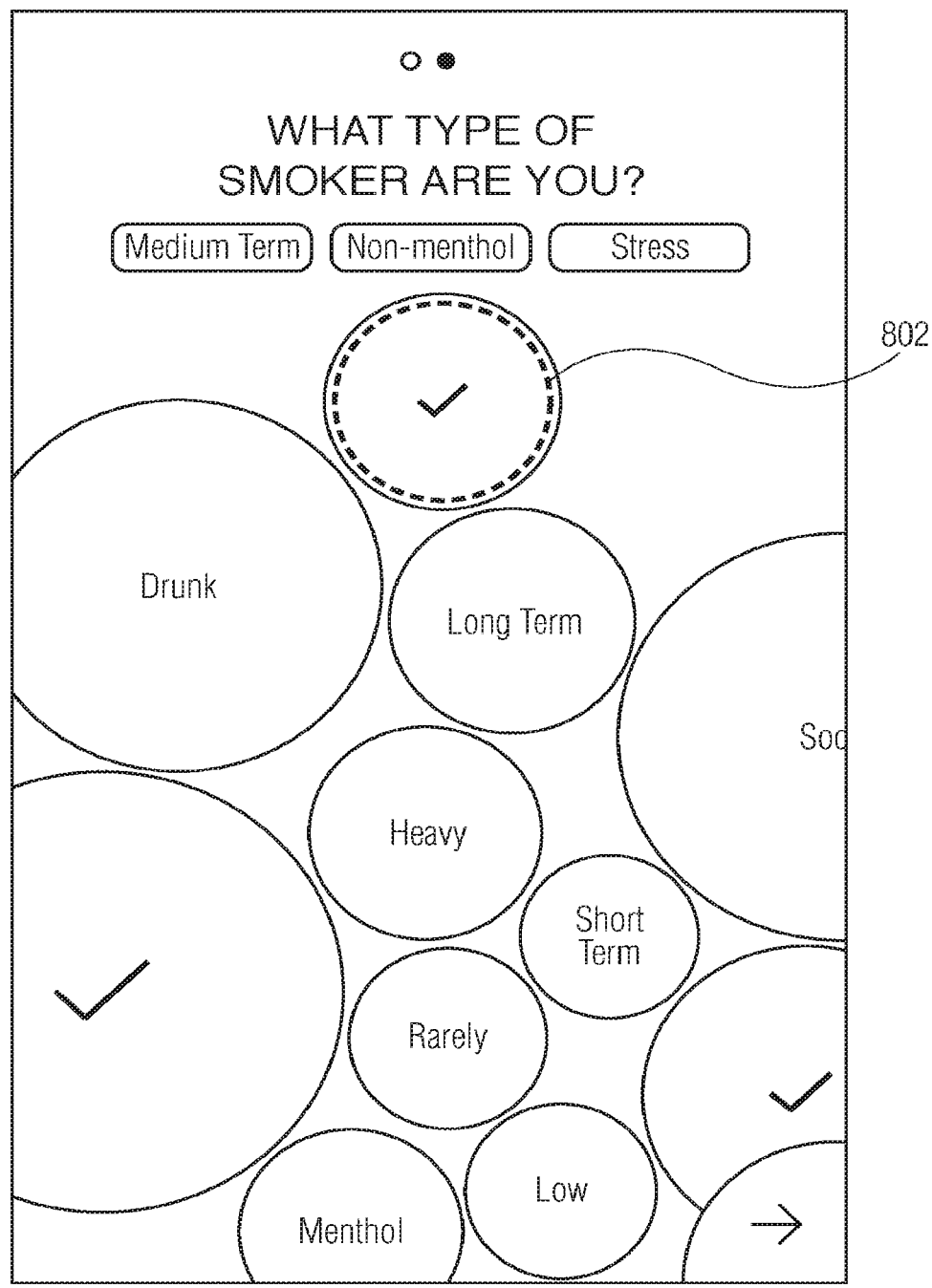
FIG. 8A is a block diagram illustrating a graphical user interface, according to example embodiments.

FIG. 8A is a block diagram illustrating an exemplary graphical user interface (GUI) 800, according to example embodiments. GUI 800 may be generated by organization computing system 104. Organization computing system 104 may provide GUI 800 to client device 106 via application 112. Client device 106 may render and display GUI 800.

GUI 800 may be representative of a smoking cessation initialization screen. For example, via GUI 800, users can provide input directed to the type of smoke the user is. GUI 800 may include one or more graphical elements 802. Each graphical element 802 may be representative of a category of smoker associated with the user. In some embodiments, a user may select multiple graphical elements 802 to provide organization computing system with a better overview of the user's smoking habits. Exemplary options may include, but are not limited to: long term smoker, heavy smoker, short term smoker, rarely, low smoker, menthol smoker, drunk smoker, social smoker, and the like.

Figure 8B:
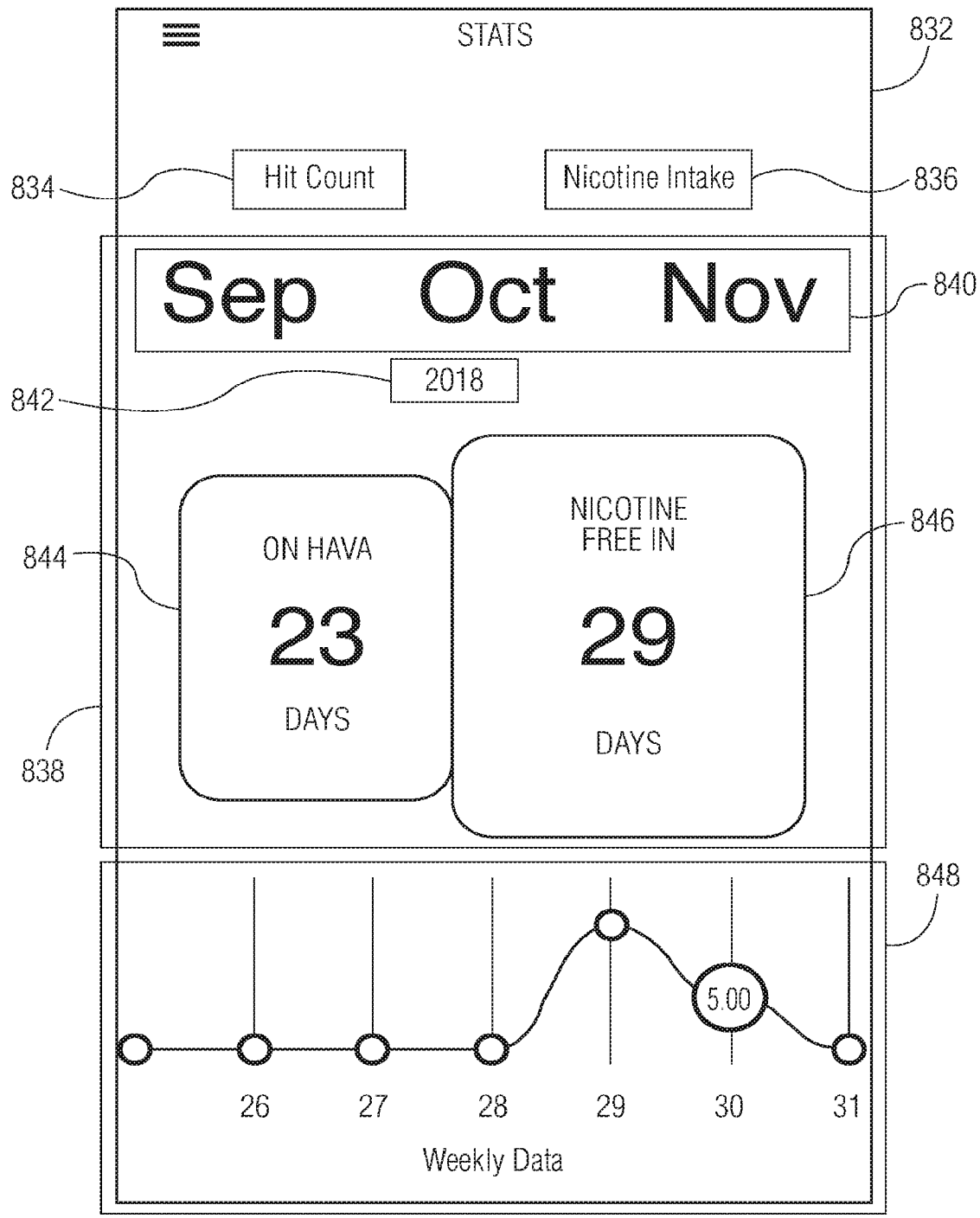
FIG. 8B is a block diagram illustrating a graphical user interface, according to example embodiments.

FIG. 8B is a block diagram illustrating an exemplary graphical user interface (GUI) 830, according to example embodiments. GUI 830 may be generated by organization computing system 104. Organization computing system 104 may provide GUI 830 to client device 106 via application 112. Client device 106 may render and display GUI 830.

GUI 830 may be representative of a screen that provides the user with smoking cessation plan statistics. For example, GUI 830 may include one or more graphical elements 834, 836, 838, and 848. Graphical element 834 may correspond to statistics associated with a hit count (i.e., the number of times a user used vaporization device 102). Graphical element 836 may correspond to statistics associated with the user's nicotine intake (i.e., how much nicotine the user is inhaling from vaporization device 102). As illustrated, the user has selected graphical element 834 associated with hit count statistics.

Graphical element 838 may include one or more graphical elements 840-846 associated with graphical element 834. Graphical element 842 may allow the user to select a year for which to view statistics. Graphical element 840 may allow the user to select a month for which to view statistics. Graphical element 844 may include one or more statistics directed to how long the user has been on the smoking cessation plan. As illustrated, this particular user has been on the plan for 23 days. Graphical element 846 may include one or more statistics directed to the goal of the individual. For example, as illustrated, this particular user will be (or should be) nicotine free in 29 days, based on the generated smoking cessation plan.

Graphical element 848 may provide weekly and/or daily data associated with graphical element 834. For example, graphical element 848 may be representative of a line graph that illustrates the user's weekly and/or daily hit count data. As illustrated, on Oct. 30, 2018, the user took 5 hits from vaporization device 102.

Figure 9:
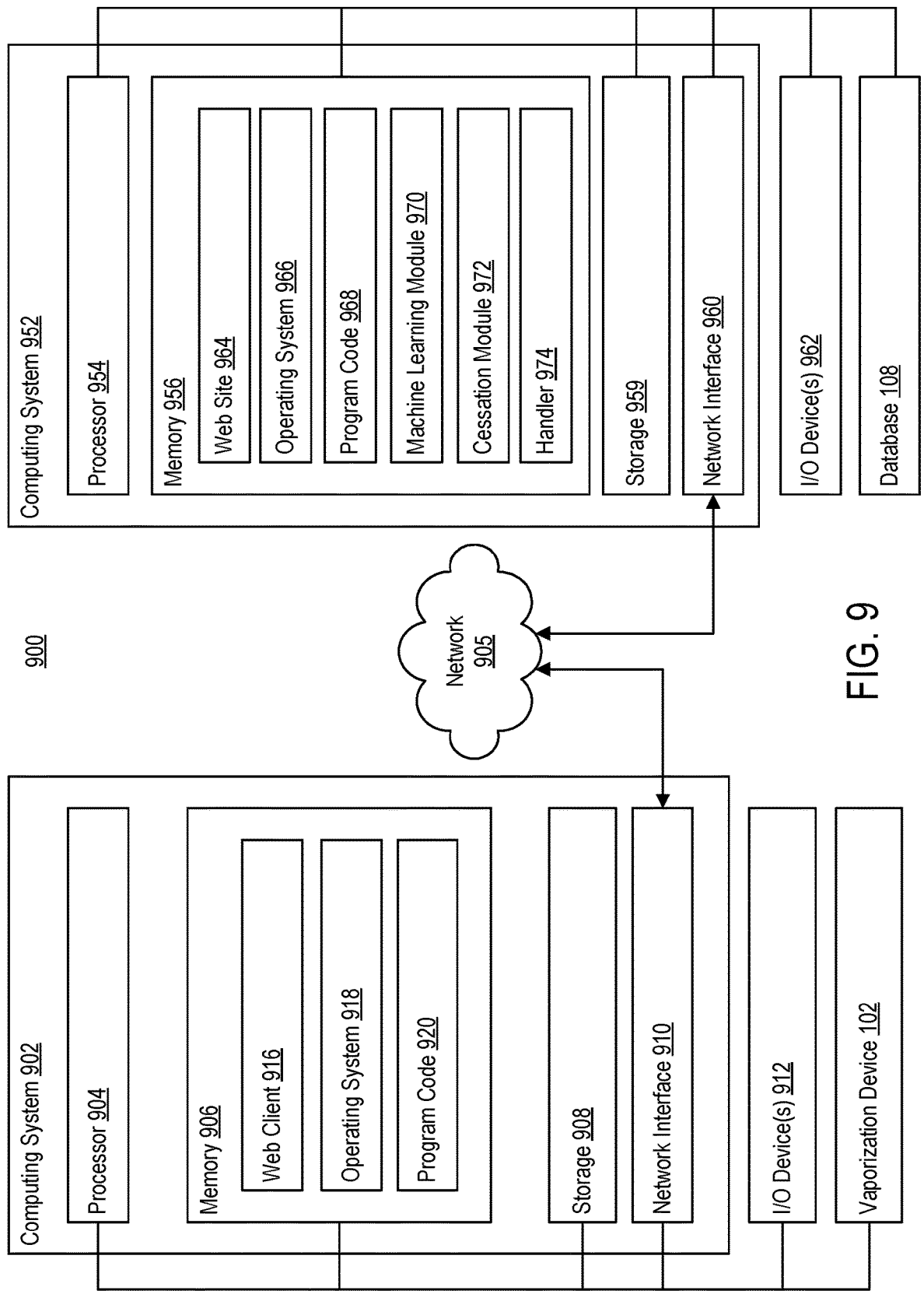
FIG. 9 is a block diagram illustrating a computing environment, according to example embodiments.

FIG. 9 is a block diagram illustrating an exemplary computing environment 900, according to some embodiments. Computing environment 900 includes computing system 902 and computing system 952. Computing system 902 may be representative of client device 106. Computing system 752 may be representative of organization computing system 104.

Computing system 902 may include a processor 904, a memory 906, a storage 908, and a network interface 910. In some embodiments, computing system 902 may be coupled to one or more I/O device(s) 912 (e.g., keyboard, mouse, etc.) and vaporization device 102. In some embodiments, computing system 902 may communicate with vaporization device 102 via network 905.

Processor 904 may retrieve and execute program code 920 (i.e., programming instructions) stored in memory 906, as well as stores and retrieves application data. Processor 904 may be included to be representative of a single processor, multiple processors, a single processor having multiple processing cores, and the like. Network interface 910 may be any type of network communications allowing computing system 902 to communicate externally via computing network 905. For example, network interface 710 is configured to enable external communication with computing system 952.

Storage 908 may be, for example, a disk storage device. Although shown as a single unit, storage 908 may be a combination of fixed and/or removable storage devices, such as fixed disk drives, removable memory cards, optical storage, network attached storage (NAS), storage area network (SAN), and the like.

Memory 906 may include application 916, operating system 918, program code 920, and messaging application 922. Program code 920 may be accessed by processor 904 for processing (i.e., executing program instructions). Program code 920 may include, for example, executable instructions for communicating with computing system 952 to display one or more pages of website 964. As another example, processor 904 may access program code 920 to perform operations for implementing a smoking cessation plan. In another example, processor 904 may access program code 920 to perform operations for selectively providing adjusting power delivered to each heating coil in vaporizer device 102. Application 916 may enable a user of computing system 902 to access a functionality of computing system 952. For example, application 916 may access content managed by computing system 952, such as website 964. The content that is displayed to a user of computing system 902 may be transmitted from computing system 952 to computing system 902, and subsequently processed by application 916 for display through a graphical user interface (GUI) of computing system 902

Computing system 952 may include a processor 954, a memory 956, a storage 958, and a network interface 960. In some embodiments, computing system 952 may be coupled to one or more I/O device(s) 962. In some embodiments, computing system 952 may be in communication with database 108.

Processor 954 may retrieve and execute program code 968 (i.e., programming instructions) stored in memory 956, as well as stores and retrieves application data. Processor 954 is included to be representative of a single processor, multiple processors, a single processor having multiple processing cores, and the like. Network interface 960 may be any type of network communications enabling computing system 952 to communicate externally via computing network 905. For example, network interface 960 allows computing system 952 to communicate with computer system 902.

Storage 958 may be, for example, a disk storage device. Although shown as a single unit, storage 958 may be a combination of fixed and/or removable storage devices, such as fixed disk drives, removable memory cards, optical storage, network attached storage (NAS), storage area network (SAN), and the like.

Memory 956 may include website 964, operating system 966, program code 968, machine learning module 970, cessation module 972, and handler 974. Program code 968 may be accessed by processor 954 for processing (i.e., executing program instructions). Program code 968 may include, for example, executable instructions configured to perform steps discussed above in conjunction with FIGS. 7A and 7B. As an example, processor 954 may access program code 968 to perform operations for generating a smoking cessation plan. In another example, processor 954 may access program code 968 to perform operations adjusting a smoking cessation plan based on usage information associated with each user. Website 964 may be accessed by computing system 902. For example, website 964 may include content accessed by computing system 902 via a web browser or application.

Cessation module 972 may be configured to communicate with client device 106. In some embodiments, cessation module 972 may be configured to communicate with vaporization device 102. Cessation module 972 may receive usage information from vaporization device 102. Cessation module 972 may work in conjunction with machine learning module 970 to generate a smoking cessation plan for each user based, in part, on user input and usage information. For example, cessation module 972 may work in conjunction with machine learning module 970 to generate a cessation plan that includes a ratio of nicotine-containing substance to non-nicotine-containing substance to deliver to a user. Based off received usage information, cessation module 972 may work in conjunction with machine learning module 970 to update the cessation plan for each user.

Machine learning module 970 may include one or more instructions to train a prediction model used by cessation module 972. To train the prediction model, machine learning module 970 may receive, as input, usage activity of each user. In some embodiments, machine learning module 970 may further receive, as input, one or more parameters specified by each user via application 916 executing on computing system 902. Machine learning module 970 may implement one or more machine learning algorithms to train the prediction model. For example, machine learning module 970 may use one or more of a decision tree learning model, association rule learning model, artificial neural network model, deep learning model, inductive logic programming model, support vector machine model, clustering mode, Bayesian network model, reinforcement learning model, representational learning model, similarity and metric learning model, rule based machine learning model, and the like.

Account handler 974 may be configured to manage an account associated with each user. For example, account handler 974 may be configured to communicate with database 108. For example, account handler 974 may be configured to update each user profile stored in database 108.

FIG. 10A illustrates a system bus computing system architecture 1000, according to example embodiments. System 1000 may be representative of at least a portion of computing system 110 in vaporization device 102. One or more components of system 1000 may be in electrical communication with each other using a bus 1005. System 1000 may include a processing unit (CPU or processor) 1010 and a system bus 1005 that couples various system components including the system memory 1015, such as read only memory (ROM) 1020 and random access memory (RAM) 1025, to processor 1010. System 1000 can include a cache of high-speed memory connected directly with, in close proximity to, or integrated as part of processor 1010. System 1000 can copy data from memory 1015 and/or storage device 1030 to cache 1012 for quick access by processor 1010. In this way, cache 1012 may provide a performance boost that avoids processor 1010 delays while waiting for data. These and other modules can control or be configured to control processor 1010 to perform various actions. Other system memory 1015 may be available for use as well. Memory 1015 may include multiple different types of memory with different performance characteristics. Processor 1010 can include any general purpose processor and a hardware module or software module, such as service 1 1032, service 2 1034, and service 3 1036 stored in storage device 1030, configured to control processor 1010 as well as a special-purpose processor where software instructions are incorporated into the actual processor design. Processor 1010 may essentially be a completely self-contained computing system, containing multiple cores or processors, a bus, memory controller, cache, etc. A multi-core processor may be symmetric or asymmetric.

To enable user interaction with the computing device 1000, an input device 1045 can represent any number of input mechanisms, such as a microphone for speech, a touch-sensitive screen for gesture or graphical input, keyboard, mouse, motion input, speech and so forth. An output device 1035 can also be one or more of a number of output mechanisms known to those of skill in the art. In some instances, multimodal systems can enable a user to provide multiple types of input to communicate with computing device 1000. Communications interface 1040 can generally govern and manage the user input and system output. There is no restriction on operating on any particular hardware arrangement and therefore the basic features here may easily be substituted for improved hardware or firmware arrangements as they are developed.

Storage device 1030 may be a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1025, read only memory (ROM) 1020, and hybrids thereof.

Storage device 1030 can include services 1032, 1034, and 1036 for controlling the processor 1010. Other hardware or software modules are contemplated. Storage device 1030 can be connected to system bus 1005. In one aspect, a hardware module that performs a particular function can include the software component stored in a computer-readable medium in connection with the necessary hardware components, such as processor 1010, bus 1005, display 1035, and so forth, to carry out the function.

FIG. 10B illustrates a computer system 1050 having a chipset architecture that may represent at least a portion of computing system 110 of vaporization device 102. Computer system 1050 may be an example of computer hardware, software, and firmware that can be used to implement the disclosed technology. System 1050 can include a processor 1055, representative of any number of physically and/or logically distinct resources capable of executing software, firmware, and hardware configured to perform identified computations. Processor 1055 can communicate with a chipset 1060 that can control input to and output from processor 1055. In this example, chipset 1060 outputs information to output 1065, such as a display, and can read and write information to storage device 1070, which can include magnetic media, and solid state media, for example. Chipset 1060 can also read data from and write data to RAM 1075. A bridge 1080 for interfacing with a variety of user interface components 1085 can be provided for interfacing with chipset 1060. Such user interface components 1085 can include a keyboard, a microphone, touch detection and processing circuitry, a pointing device, such as a mouse, and so on. In general, inputs to system 1050 can come from any of a variety of sources, machine generated and/or human generated.

Chipset 1060 can also interface with one or more communication interfaces 1090 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 1055 analyzing data stored in storage 1070 or 1075. Further, the machine can receive inputs from a user through user interface components 1085 and execute appropriate functions, such as browsing functions by interpreting these inputs using processor 1055.

It can be appreciated that example systems 1000 and 1050 can have more than one processor 1010 or be part of a group or cluster of computing devices networked together to provide greater processing capability.

While the foregoing is directed to embodiments described herein, other and further embodiments may be devised without departing from the basic scope thereof. For example, aspects of the present disclosure may be implemented in hardware or software or a combination of hardware and software. One embodiment described herein may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory (ROM) devices within a computer, such as CD-ROM disks readably by a CD-ROM drive, flash memory, ROM chips, or any type of solid-state non-volatile memory) on which information is permanently stored; and (ii) writable storage media (e.g., floppy disks within a diskette drive or hard-disk drive or any type of solid state random-access memory) on which alterable information is stored. Such computer-readable storage media, when carrying computer-readable instructions that direct the functions of the disclosed embodiments, are embodiments of the present disclosure.

It will be appreciated to those skilled in the art that the preceding examples are exemplary and not limiting. It is intended that all permutations, enhancements, equivalents, and improvements thereto are apparent to those skilled in the art upon a reading of the specification and a study of the drawings are included within the true spirit and scope of the present disclosure. It is therefore intended that the following appended claims include all such modifications, permutations, and equivalents as fall within the true spirit and scope of these teachings.

What is claimed:

1. A vaporization device, comprising:
  a first portion comprising:
    a first body defining an interior volume, the first body comprising a top portion and a bottom portion;
    a first pod configured to hold a non-nicotine-containing liquid, the first pod configured to be disposed in the interior volume,
    a second pod configured to hold a nicotine-containing liquid, the second pod configured to be disposed in the interior volume adjacent the first pod,
    an inhalation opening formed in the top portion of the body, and
    a mixing chamber formed in the first portion between the first pod and the second pod, the mixing chamber in fluid communication with the inhalation opening formed in the top portion of the first body, the mixing chamber physically separating the first pod from the second pod, the mixing chamber running in a vertical direction from the inhalation opening formed in the top portion of the first body to the bottom portion of the first body; and
  a second portion selectively coupled with the first portion, the second portion comprising:
    a second body comprising a second interior volume, and
    a computing system disposed within the second interior volume, the computing system configured to vary a ratio of the non-nicotine-containing liquid to the nicotine-containing liquid delivered to a user in accordance with a customized smoking cessation plan of the user.

2. The vaporization device of claim 1, wherein the first body further comprises:
  a first heating apparatus dedicated to the first pod; and
  a second heating apparatus dedicated to the second pod.

3. The vaporization device of claim 2, wherein the first heating apparatus comprises:
  a heating coil configured to interface with an electric contact, the heating coil configured to vaporize the non-nicotine-containing liquid in the first pod.

4. The vaporization device of claim 2, wherein the second heating apparatus comprises:
  a heating coil configured to interface with an electric contact, the heating coil configured to vaporize the nicotine-containing liquid in the second pod.

5. The vaporization device of claim 1, wherein the computing system is configured to interface with an external computing device over one or more wired or wireless networks.

6. The vaporization device of claim 1, wherein the computing system is configured to:

initiate a learning process in which a machine learning model learns smoking behaviors of the user.

7. The vaporization device of claim 6, wherein the customized smoking cessation plan is based on the learned smoking behaviors of the user.

8. A vaporization device, comprising:
a first portion comprising:
   a first body defining an interior volume, the first body comprising a top portion and a bottom portion,
   a first pod configured to hold a first liquid, the first pod configured to be disposed in the interior volume,
   a second pod configured to hold a second liquid, the second pod configured to be disposed in the interior volume,
   an inhalation opening formed in the top portion of the first body,
   a mixing chamber formed in the first portion between the first pod and the second pod, the mixing chamber in fluid communication with the inhalation opening formed in the top portion of the first body, the mixing chamber physically separating the first pod from the second pod, the mixing chamber running in a vertical direction from the inhalation opening formed in the top portion of the first body to the bottom portion of the first body,
   a first heating apparatus dedicated to the first pod, the first heating apparatus configured to vaporize the first liquid, and
   a second heating apparatus dedicated to the second pod, the second heating apparatus configured to vaporize the second liquid; and
a second portion selectively coupled with the first portion, the second portion comprising:
   a second body comprising a second interior volume, and
   a computing system disposed within the second interior volume, the computing system configured to vary a ratio of the first liquid to the second liquid delivered to a user in accordance with a customized dosage plan of the user.

9. The vaporization device of claim 8, wherein the first heating apparatus comprises:
a heating coil configured to interface with an electric contact, the heating coil configured to vaporize the first liquid in the first pod.

10. The vaporization device of claim 8, wherein the second heating apparatus comprises:
a heating coil configured to interface with an electric contact, the heating coil configured to vaporize the second liquid in the second pod.

11. The vaporization device of claim 8, wherein the computing system is configured to interface with an external computing device over one or more wired or wireless networks.

12. The vaporization device of claim 8, wherein the computing system is configured to:
initiate a learning process in which a machine learning model learns consumption behaviors of the user.

13. The vaporization device of claim 12, wherein the customized dosage plan is based on the learned consumption behaviors of the user.

14. A vaporization device, comprising:
a body defining an interior volume, the body comprising a top portion and a bottom portion;
a first pod disposed in the interior volume, the first pod configured to hold a first liquid;
a second pod disposed in the interior volume, the second pod configured to hold a second liquid;
an inhalation opening formed in the top portion of the body;
a mixing chamber formed between the first pod and the second pod, the mixing chamber in fluid communication with the inhalation opening formed in the top portion of the body, the mixing chamber physically separating the first pod from the second pod, the mixing chamber running in a vertical direction from the inhalation opening formed in the top portion of the body to the bottom portion of the body;
a first heating apparatus dedicated to the first pod, the first heating apparatus configured to vaporize the first liquid;
a second heating apparatus dedicated to the second pod, the second heating apparatus configured to vaporize the second liquid; and
a computing system configured to:
   deliver a dosage amount of vapor to a user by:
      causing the first heating apparatus to vaporize a first amount of the first liquid, and
      causing the second heating apparatus to vaporize a second amount of the second liquid, wherein the first amount of the first liquid and the second amount of the second liquid are based on a customized dosage plan of the user.

15. The vaporization device of claim 14, further comprising:
an electric contact configured to receive current from the computing system;
a heating coil configured to interface with the electric contact, the heating coil configured to vaporize the first liquid in the first pod;
a second electric contact configured to receive a second current from the computing system; and
a second heating coil configured to interface with the second electric contact, the second heating coil configured to vaporize the second liquid in the second pod.

16. The vaporization device of claim 14, wherein the computing system is further configured to:
cause a machine learning model to learn consumption habits of the user.

17. The vaporization device of claim 16, wherein the dosage amount is a predetermined ratio of the first liquid to the second liquid based on the learned consumption habits of the user.

18. The vaporization device of claim 17, wherein the computing system is further configured to:
track usage statistics associated with the user, the usage statistics comprising an amount of vapor consumed by the user.

19. The vaporization device of claim 18, wherein the computing system is further configured to:
adjust the predetermined ratio of the first liquid to the second liquid based on the usage statistics deviating a threshold amount from the learned consumption habits of the user.

* * * * *